US009115181B2

(12) United States Patent
Van Alstine et al.

(10) Patent No.: US 9,115,181 B2
(45) Date of Patent: Aug. 25, 2015

(54) SEPARATION METHOD USING SINGLE POLYMER PHASE SYSTEMS

(75) Inventors: James Van Alstine, Stockholm (SE); Jamil Shanagar, Uppsala (SE); Rolf Hjorth, Uppsala (SE); Martin Hall, Uppsala (SE); Camilla Estmer Nilsson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 938 days.

(21) Appl. No.: 13/143,560

(22) PCT Filed: Jan. 7, 2010

(86) PCT No.: PCT/SE2010/050008
§ 371 (c)(1),
(2), (4) Date: Sep. 26, 2011

(87) PCT Pub. No.: WO2010/080062
PCT Pub. Date: Jul. 15, 2010

(65) Prior Publication Data
US 2012/0010390 A1    Jan. 12, 2012

(30) Foreign Application Priority Data
Jan. 8, 2009   (SE) ...................................... 0900014

(51) Int. Cl.
| | |
|---|---|
| *A23J 1/00* | (2006.01) |
| *C07K 1/00* | (2006.01) |
| *C07K 14/00* | (2006.01) |
| *C07K 16/00* | (2006.01) |
| *C07K 17/00* | (2006.01) |
| *C07K 1/14* | (2006.01) |
| *C07K 1/36* | (2006.01) |
| *C07K 16/04* | (2006.01) |
| *C07K 16/06* | (2006.01) |

(52) U.S. Cl.
CPC . *C07K 16/00* (2013.01); *C07K 1/14* (2013.01); *C07K 1/36* (2013.01); *C07K 16/04* (2013.01); *C07K 16/065* (2013.01); *C07K 2317/10* (2013.01)

(58) Field of Classification Search
None
See application file for complete search history.

(56) References Cited

U.S. PATENT DOCUMENTS

| | | | | |
|---|---|---|---|---|
| 5,429,746 | A * | 7/1995 | Shadle et al. .................. | 210/635 |
| 6,454,950 | B1 * | 9/2002 | Tjerneld et al. ............... | 210/734 |
| 8,268,915 | B2 * | 9/2012 | Johansson et al. ............. | 524/24 |
| 2003/0036192 | A1 * | 2/2003 | Singh .......................... | 435/297.2 |
| 2008/0293926 | A1 * | 11/2008 | Hallgren et al. .............. | 530/427 |
| 2010/0174052 | A1 * | 7/2010 | Hjorth et al. ................ | 530/388.1 |

FOREIGN PATENT DOCUMENTS

| | | |
|---|---|---|
| WO | WO 2008/156409 | 12/2008 |
| WO | WO 2008/156410 | 12/2008 |
| WO | WO 2008156409 A1 * | 12/2008 |

OTHER PUBLICATIONS

Johansson, Hans-Olof, et al., "Thermoseparating Water/Polymer System: A Novel One-Polymer Aqueous Two-Phase System for Protein Purification", Biotechnology and Bioengineering, (1999), 66(84):247-257.
Azevedo, A. M., et al., "Integrated Process for the Purification of Antibodies Combining Aqueous Two-Phase Extraction, Hydrophobic Interaction Chromatography and Size-Exclusion Chromatography", Journal of Chromatography A, (2008), 1213:154-161.
Lu, J., et al., "Preparation and Application of Novel EOPO-IDA-Metal Polymer as Recyclable Metal Affinity Ligand in Aqueous Two-Phase Systems", Ind. Eng. Chem. Res., (2006), 45:1774-1779.
Azevedo, A. M., et al., "Chromatography-Free Recovery of Biopharmaceuticals Through Aqueous Two-Phase Processing", Trends in Biotechnology, (2009), 27(4):240-247.
Trindade, I. P., et al., "Purification of Plasmid DNA Vectors by Aqueous Two-Phase Extraction and Hydrophobic Interaction Chromatography", Journal of Chromatography A, (2005), 1082:176-184.
Pereira, M., et al., "Aqueous Two-Phase Extraction Using Thermoseparating Polymer: A New System for the Separation of Endo-Polygalacturonase", Biochemical Engineering Journal, (2003), 15:131-138.
Johansson, H.-O., et al., "Temperature-Induced Phase Partitioning of Peptides in Water Solutions of Ethylene Oxide and Propylene Oxide Random Copolymers", Biochimica et Biophysica Acta, (1997), 1335:315-325.
Johansson, H.-O., et al., "Driving Forces for Phase Separation and Partitioning in Aqueous Two-Phase Systems", Journal of Chromatography B, (1998), 711:3-17.
Azevedo, A. M., et al., "Optimisation of Aqueous Two-Phase Extraction of Human Antibodies", Journal of Biotechnology, (2007), 132:209-217.
Alred, P., et al., Journal of Chromatography A, vol. 659, No. 2, 1994, pp. 289-298.
Harris, P., et al., Bioseparation, vol. 2, No. 4, 1991, pp. 237-246.
Persson, J., et al., Journal of Chromatography B, vol. 711, No. 1-2, 1998, pp. 97-109.
Campese, G., et al., Brazilian Journal of Chemical Engineering, vol. 20, No. 3, 2003, pp. 335-337.

* cited by examiner

*Primary Examiner* — Daniel E Kolker
*Assistant Examiner* — James Rogers
(74) *Attorney, Agent, or Firm* — Parks Wood LLC; Collen A. Beard, Esq.

(57) ABSTRACT

The present invention relates to a process of enriching one target compound from a liquid, which process comprises at least one step of isolation performed by differentially partitioning between two aqueous phases. In the present invention the phases are formed by adding a thermally responsive, self-associating (i.e. clouding) hydrophilic polymer, and if needed some additional salts, to an aqueous biotechnical solution (such as a fermentation sample or bioseparation process stream) under thermal and other conditions where the solution separates into a one polymer, two-phase system with one phase enriched in the polymer. The target compound is to be found in the phase not enriched in the polymer, while a significant though varying percentage of contaminants may differentially partition to the phase interface or the polymer enriched phase. With minor or no modification the target containing phase solution can be further processed via standard unit operations such as precipitation, chromatography, and filtration to further purify target and remove any residual polymer.

23 Claims, 11 Drawing Sheets

SEPARATION METHOD USING SINGLE POLYMER PHASE SYSTEMS

CROSS-REFERENCE TO RELATED APPLICATIONS

This application is a filing under 35 U.S.C. §371 and claims priority to international patent application number PCT/SE2010/050008 filed Jan. 7, 2010, published on Jul. 15, 2010 as WO 2010/080062, which claims priority to application number 0900014-2 filed in Sweden on Jan. 8, 2009.

TECHNICAL FIELD

The present invention relates to a process of enriching one target compound from a liquid, which process comprises at least one step of isolation performed by differentially partitioning between two aqueous phases. It appears particularly well suited to antibody or antibody derived targets, and could also be suitable for other applications such as in viral vaccine processing.

BACKGROUND OF THE INVENTION

The biotechnical revolution, including development of modern biopharmaceuticals and mapping of the human genome, has been made possible due to development of separation methods such as chromatography and electrophoresis. Such methods can be used in small scale as well as in large scale, and are known as flexible methods, being useful for a variety of substances including biological substances. However, they are demanding both technically and in terms of equipment. In addition, scaling of some processes such as preparative electrophoresis results in a need for more complicated equipment due to nonlinear scaling of heating and cooling requirements. Such complications also hinder modelling of such methods and their optimisation via (small volume, microtiter) high throughput screening methods.

Partitioning between the phases in aqueous polymer phase systems is an alternative method, which has been studied since the 1950's but whose commercial application has been severely restrained by lack of economically feasible (inexpensive) phase systems offering good capacity (target solubility). Together with separation methods such as flocculation, crystallization and size exclusion; partitioning is considered a classic separation technique. It is related to differentially distributing a target and other substances between two phases. The term "partitioning" can refer to (a) liquid-solid partition such as in classic capture chromatography, (b) partitioning between two or more liquid phases (biphasic and multiphase system, respectively), (c) partitioning between a mobile liquid phase and another liquid phase immobilized at the surface of a solid phase support, and (d) partitioning of particles between a liquid phase and the phase interface between two phases. For the purposes of this patent application, partition and partitioning refer to situations such as b, c or d i.e. partitioning between liquid phases. In this definition target capacity is not as much a function of (solid) phase surface area as much as liquid phase volumes. As a result capacities can be very high (see below). Partition is typically expressed as a coefficient (K) related to the concentration in one phase versus another and for solutes K generally follows the Brønsted equation. Thus K is expected to vary exponentially with various types of interactions such as electrostatic and/or hydrophobic interactions, and also to be sensitive to solute size i.e. the area of interaction with liquid phases. In the case of interfacial partition, where particles may be held at a liquid-liquid phase interface by interfacial tension, K is expected to vary exponentially with interfacial tension, as well as phase compositional factors.

Classic liquid-liquid two-phase systems are organic and aqueous two phase systems which normally have significant polarity differences between the phases, as well as significant interfacial tension. Such systems are not very useful for biologicals, such as proteins or cells, as they tend to be denatured by significantly apolar solutions and shear damage related to mixing of phase systems with significant interfacial tension. More useful for biologicals are low tension, aqueous polymer two phase-systems. It is well recognized that the latter may contain some added organic solvents, e.g. ethanol, or other organic additives added to enhance target solubility, reduce liquid phase polarity, reduce foaming, act as bactericidal agents, etc.

Polymer two-phase systems can be formed by mixing certain hydrophilic and typically neutral polymers in aqueous solution. These include dextran (polyglucose) and poly(ethylene glycol) (PEG); as well as polysucrose (such as Ficoll™) and PEG; or linear polyacrylamide and PEG. Typical concentrations of each polymer are 5 to 10% w/w. At such concentrations, entropic and other forces tend to drive the formation of two phases both of which are typically greater than 90% (w/w) water but show subtle differences in polarity, hydrogen bond character, freezing point, etc. The phases are typically enriched in one polymer and have low interfacial tension. Phase density differences drive the phases to separate by gravity or centrifugation. In the biotechnical field, one advantage of the PEG and Dextran type of two-phase system is that target proteins may partition in favour of the PEG-enriched, less dense, upper phase while cell debris and some contaminants may partition (or sediment) to the interface or complementary lower phase.

Independent of the challenging of adding and then removing two polymers from a bioprocess stream the major drawback to dextran and PEG and similar two-polymer phase systems is the cost of the polymers. This is especially true for the dextran, a natural bioproduct which must itself be purified for use in bioprocess phase systems. In an effort to reduce such costs scientists have investigated two paths. The first is to replace dextran with starch or other less expensive polymers. However such polymers often are less pure, less controlled in MW, form more viscous phases and come with their own unique challenges (Josefine Persson, Dana C. Andersen, Philip M. Lester, Biotechnology and Bioengineering, vol. 90, (2005) 442-451). The other approach has been to work with two phase systems formed by combining relatively high concentrations of PEG (10% w/w) and salts such as potassium sulphate (3% w/w). In regard to protein partition in such systems see Andrews, Nielsen, Asenjo, 1996. and Azevedo et al., 2007 (discussed in more detail below) while for recent review related to plasmid partition see F. Rahimpour, F. Feyzi, S. Maghsoudi, R. Hatti-Kaul, Biotechnology and Bioengineering, 95, 627-637, 2006.) Unfortunately the increased PEG and salt concentrations create challenges which negatively impact process costs. These include viscous phases, salt reagent costs, salt disposal and equipment corrosion challenges, as well as target solubility issues which relate to capacity. For example antibody capacity in these systems is often 1 g/L which means (clarified) fermentation broth containing expressed antibody at 10 g/L would have to be diluted ten fold prior to partitioning. It also means that if the phase systems cost five dollars a liter to formulate then they add at least five dollars a gram to the cost of goods. Such dilution and related increases in process volumes, process times and costs are prohibitive.

Some hydrophilic polymers exhibit inverse thermal solubility such that as temperature is raised above a certain cloud temperature (Tc) which is related to a polymer's lower critical solubility temperature (LCST), they self associate and start to form a unique polymer rich phase. Common literature offers several examples of such polymers including copolymer or block copolymers formed with mixtures of ethylene oxide (EO) and propylene oxide (PO) monomeric groups, so called EOPO polymers, polysaccharides modified with EO, PO or similar groups (e.g. ethylhydroxyethylcellulose or EHEC), or polymers formed using N-isopropylacrylamide (NIPAAM). Whereas the Tc for PEG (polymerised EO) in dilute buffered solution is around 100° C., and thus unsuitable for most biotechnical applications, the Tc for EOPO and NIPAAM polymers is often in more biotechnically useful range of 20 to 40° C., depending on solution salt composition and other factors. In addition to thermoresponsive polymers some hydrophilic polymers exhibit pH dependent self association (e.g. WO 2004/082801 A1). WO 2004/020629 (Tjerneld) relates to the use of the EOPO polymers' reverse thermal solubility to further facilitate the separation of plasmids already partitioned in a two polymer phase system. At room temperature the two-polymer, two phase system formed with EOPO and dextran polymers forms in same manner as PEG and dextran system. The less dense EOPO-enriched upper phase is isolated from the EOPO and dextran polymer aqueous two-phase system. The temperature of the EOPO-enriched phase is then raised to approximately 37° C. (i.e. above Tc) so that the upper phase undergoes further phase separation into a water-enriched phase and a self-associated EOPO polymer-enriched phase. Advantageously, the water-enriched phase should contain the desired target. In general, these kinds of EOPO and dextran systems offer advantages in terms of phase polymer component recycling and design of efficient two-stage partition separation process. However, a drawback is again the cost involved in system formulation using the biologically derived and costly dextran polymer. Less expensive polymers such as starch polymers may replace dextran in such systems (Persson et al, 2005) but there are still challenges associated with having to add then remove two polymers from the process stream.

In the above literature examples, as in the general literature, phase systems are used to purify targets from clarified feed formed by subjecting phase fermentation broth containing intact or lysed cells and cell debris to centrifugation.

In the biotechnical field, aqueous polymer two phase systems, formed with two polymers or with one polymer in presence of significant added salt are of general interest. This is because they are easily utilised in small as well as larger scale separations, without loss of efficiencies or dramatic changes in costs when scaling up to the larger volumes. Also, any standard separation approach, such as charge-based, hydrophobicity-based, affinity-based, or size-based separation, can be performed within a polymer two phase system. In general many undesired components, such as cell debris, endotoxins, nucleic acids, virus, will tend to appreciably partition to the lower (dextran-rich or salt rich, respectively) phase in a PEG and dextran, or a PEG and salt two phase system. Thus, if a system can be found which provides for good target partition into the upper (PEG-rich) phase an effective primary separation and target concentration can be obtained. However four major hurdles will still remain in terms of capacity (i.e. solubility), phase component cost, phase component removal, and effect of phase components on other (downstream) unit operations and equipment. The latter particularly inhibits easy incorporation of some phase systems, as upstream unit operations, in existing standard processes.

In efforts to overcome drawbacks related to interfacing in standard chromatographic and/or filtration processing, and to overcome the limitations of a single theoretical partition step per unit operation, liquid-liquid partitioning two phase systems such as PEG-dextran or PEG-salt have been adapted to chromatographic uses by immobilising one phase on a chromatographic or other solid support capable of preferentially wetting that phase. The complementary phase is then pumped through the column offering repeated opportunities for equilibration between the mobile and stationary phase. This was commercially exploited by W. Müller et al. at E. Merck, Darmstadt in the 1980's (U.S. Pat. No. 4,756,834).

Various combinations of the above approaches and other phase forming polymers are possible. U.S. Pat. No. 5,093,254 (Giuliano et al) relates to an aqueous two-phase protein partitioning system which employs polyvinylpyrrolidone (PVP) as the upper phase and maltodextrin as the lower phase and provides a low-cost system for protein partitioning. The system can also be employed with certain derivatives of chlorotriazine dyes, which bind in a noncovalent manner to the PVP and serve as a ligand for the proteins to be separated. It is stated that an advantage of this system is its cost-efficiency, as the dyes can easily be bound to the polymeric phase, without having to carry out the chromatographic and solvent extractions necessary to form the covalent bond in the PEG and hydroxypropyl starch system of the prior art.

Many modern biopharmaceuticals are based on monoclonal antibodies (typically IgG forms) or related antibody fragments (Fabs) or derivatives of antibodies. Use of phase systems for purification of antibodies has been studied for over thirty years, if one includes studies of plasma protein partitioning in dextran and PEG and related two polymer biphasic systems. Studies directed towards feasibility of large scale processing of antibodies by partitioning, using more cost effective PEG-salt and other systems have been in the literature for over a decade.

B. A. Andrews, S. Nielsen and J. A. Asenjo (Partitioning and purification of monoclonal antibodies in aqueous two-phase systems, Bioseparation 6, (1996) 306-313) investigated systems and used factorial design to find some they consider optimal for antibody partitioning such as 7% w/w PEG 1450, 14% NaPhosphate and 12% NaCl. Such systems gave antibody partition K (ratio of protein concentration in upper phase over lower phase) values of 100. They used serum albumin, transferin and some other proteins to represent process feed stream contaminants and demonstrated differential partition to that shown for antibodies. In addition they attempted small scale processing of a monoclonal antibody sample from hybridoma cell culture. As with Persson et al. 2005 and Azevedo et al., 2007, they worked with centrifuge clarified (cell free) sample solutions. In the experiments with hybridoma produced antibody sample they noted that K values obtained with pure protein samples appeared compromised by sample solution complexity. However they were able to achieve good partition of antibody into one phase, and show ability to enhance purity using multiple extractions, including those where the target molecule is partitioned into complementary phase using a system with lower NaCl.

Andrews et al. also noted what remains the main drawback to PEG salt system protein partitioning in general, and antibody partitioning in particular, which (due to the high salt concentrations) is low protein solubility (often 1 g/L). If one considers that antibodies and other recombinant proteins may be expressed at levels of 10 g/L or higher use of such systems early in separation process would entail a 10-fold increase in process volume with a several fold increase in processing scales, costs and times. In addition to these costs would be those related to salt components including salt removal and possible corrosion of pumps and other metal equipment. A decade later Azevedo et al. (Ana M. Azevedo, Paula A. J. Rosa, I. Filipa Ferreira, M. Raquel Aires-Barros, Optimisation of aqueous two-phase extraction of human antibodies, Journal of Biotechnology 132 (2007) 209-217) extended efforts to find PEG and salt systems suitable for industrial scale process of antibodies. Their optimisation methods found systems similar to those of Andrews et al. (i.e. 12% PEG 6000, 10% NaPhosphate pH 6, 15% NaCl) which when used to partially purify Mab from a concentrated (and clarified) Chinese Hampster Ovary (CHO) cell culture supernatant with total yield of 88% and from hybridoma culture supernatant with a total yield of 90%. However their target protein concentrations were still approximately 1 g/L.

More recently Aires-Barros et al (I. Filipa Ferreira, Ana M. Azevedo, Paula A. J. Rosa, M. Raquel Aires-Barros, Purification of human immunoglobulin G by thermoseparating aqueous two-phase systems, Journal of Chromatography A, 1195 (2008) 94-100) have investigated two polymer thermoseparating phase systems for antibody partitioning in systems containing UCON® EOPO 50/50 copolymers of MW 2000 to 5100 (Dow Chemical). They studied partitioning of IgG from clarified CHO culture supernatant (Ab at 0.1 g/L) between the phases in 8% w/w UCON and 5% dextran T500 systems and to enhance antibody partition into the upper (EOPO polymer-rich) phase they added 20% w/w triethylene glycol-diglutaric acid (TEG-COOH) and 10 mM NaPhosphate pH 8. Clarified supernatant could be added to systems at 50% (to achieve above final polymer and TEG-COOH concentrations). In some experiments polyclonal IgG (Gammanorm™, Octapharma AG) was added to increase target protein to approximately 1 g/L. A two step (two polymer two phase partition followed by thermoseparation of the upper phase into polymer-rich and water rich phases, see above) partition process yielded 85% of antibody (which is relatively low for a commercially attractive process) at 88% purity (which may have been aided by adding in GammaNorm). Tc occurred at approximately 50° C. which required applied heating of the phase system in the second step extraction. While these systems offer lower salt concentration they also require significant TEG-COOH as in its absence recovery yield of IgG in the top UCON-rich phase (of UCON and Dextran phase system) was lower than 50% (i.e. K<1).

In general thermoseparating phases have normally been used together with dextran (see Aires-Barros et al, above) or similar polysaccharide (Persson et al. above) in a two step process. Thus selectivity over target and contaminant protein (as well as second polymer) occurs in the first partition step, followed by use of temperature induced phase separation (of typically EOPO polymer rich phase) to isolate target and polymer into target containing aqueous phase floating on top of a self-associated polymer rich denser phase. In regard to the use of thermoseparating phases on their own (i.e. one polymer but lower salt concentration) systems the general wisdom has been that they tend to not be useful as they offer little selectivity and should be used in systems with other polymers. A distinguished international research group was led to conclude "the water EOPO system is therefore only suitable for partitioning of hydrophobic molecules (such as denatured proteins or tryptophan-rich peptides) or for solution concentration by selective water removal (similar arguments hold for the micellar two-phase systems)" (Hans-Olof Johansson, Gunnar Karlström, Folke Tjerneld, Charles A. Haynes, J. Chromatography B, 711 (1998) 3-17). In regard to such applications the effect of various salts and other additives on phase separation of another EOPO polymer (Breox 50 A 1000 a random copolymer consisting of 50% ethylene oxide and 50% propylene oxide, molecular mass number average 3900, Specialty Chemicals, Southhampton, UK). were studied by Cunha et al. (Maria Teresa Cunha, Folke Tjerneld, Joaquim M. S. Cabral, Maria Raquel Aires-Barros, Journal of Chromatography B, 711 (1998) 53-60).

Teixeira et al. (Martinha Pereira, You-Ting Wu, Armando Venancio, José Teixeira, Biochemical Engineering Journal 15 (2003) 131-138) investigated the partitioning of endo-polygalacturonase (endo-PG) in systems composed of UCON 50-HB in two-polymer systems together with polyvinylalcohol, or hydroxypropylstarch or with relatively high concentrations of ammonium sulfate. The latter system required heating to effect formation of two phases but was the most promising in terms of reagent cost and ability for reagents to be added to culture (again clarified) supernatant prior so that 70% of the final system consisted of clarified culture broth. The UCON polymer could be recycled in a three step process in which endo-PEG was concentrated ten times and 95% of enzyme activity was recovered. In regard to this work two observations are note worthy. First the 5% minimum ammonium salt concentration (50 g/L or approx. 0.38M) necessary to effect formation of two phases is still significant and required 10% UCON. Raising temperature to 40° C. only decreased these values to 3% (0.23 M) salt and 5% polymer. So the system still contained significant added salt. Secondly at temperatures above 30 degrees Texeira et al noted phase inversion in their systems so that the top, polymer poor, less-dense phase at room temperature became the bottom phase. Such effects while interesting, could pose problems in regard to large scale processing particularly in systems containing cells and cell debris which would tend to sediment. In addition to the above noted thermoseparating phase systems there are a wide range of thermoseparated micellular systems involving hydrophobically modified EOPO and similar polymers (for discussion see H.-O. Johansson et al, 1998 above). Many patents related to the above two polymer thermoseparating aqueous phase systems are currently held by G.E. Healthcare, a General Electric company.

The ability of PEG and salt two-phase systems to partition cells and cell debris to interface, and therefore for possible use of phase partitioning to effect partial clarification, has been known for some time. Köhler et al. formed 7.5% w/w PEG 1500 and 14% potassium phosphate two-phase systems directly in a bioreactor and used them to purify a recombinant protein in *E. coli* (Kristina Köhler, Björn Nilsson, Andres Veide, Recovery of extracellular human insulin-like growth factor-I and II as a fusion protein from *Escherichia coli* culture broth by aqueous two-phase extraction, Bioseparation, 3 (1992-1993) 241-250) noting approximately 90% of cells were not in the target containing phase. However batch centrifugation was still used in the process to effect complete phase separation and was advocated, in continuous centrifugation mode, for larger scale applications. Such polymer-high salt systems have much greater interfacial tension than polymer-polymer systems formed at lower salt concentration and may be expected to function to effect some clarification due to their relatively high interfacial tension. However they would supposedly still be limited in terms of capacity (target solubility) due to the high salt concentrations required. Köhler et al. noted that biomass added to system affected some partition results. Since most studies related to finding optimized systems for recombinant protein (esp. antibodies) processing have been done using clarified feed the systems found may not be optimal or even function for clarified feed. That is why several examples of unclarified feed were used in the present work.

It can be seen from the above discussion that two phase partitioning holds much promise as method for primary processing (clarification and target partial purification) of various substances such as proteins including biopharmaceuticals from complex feeds streams however to date certain challenges have not been overcome. These include cost of reagents (polymer and salts, or two polymers), capacity issues related to needed dilution of target containing process streams, possible need to add various affinity substances (e.g. TEG-COOH) to increase target partition, removal of phase system forming substances prior to or during further downstream processing steps, and modifying target containing phases to allow for further downstream processing. From the point of simplicity thermoresponsive polymer and water systems (which do not involve micelle formation or use of special hydrophobically modified thermoresponsive polymers) may be the most attractive as they are typically neutral and in some cases biocompatible. So too residual polyethoxy and other polymers in target containing phase may not only be seen as relatively inert substances. They may confer some advantages for a. further processing by multistep partitioning, b. spray drying of target containing solution (e.g. Jessica Elversson, Anna Millqvist-Fureby, Aqueous two-phase systems as a formulation concept for spray-dried protein, International Journal of Pharmaceutics 294 (2005) 73-87) and, due to their well known antifreeze and antioxidant properties, c. low temperature intermediate storage of target containing phase solution prior to further processing. However established wisdom and experience has been that their formation required relatively high polymer and salt concentrations and the phases formed offered little selectivity, required fairly high salt concentrations and might not work to effect clarification.

For many years biopharmaceutical fermentation, purification and polishing/formulation have been seen as separate process areas. A major reason for this was they often involved different unit operations and volume scales. Both of these were related to the concentration of target substance and inversely the process volumes handled in different processing stages. Thus fermentation at perhaps 1 mg/mL, purification by affinity or ion exchange raising the concentration to perhaps 30 mg/mL with polishing followed by formulation steps taking the target to 100 in liquid (mg/mL) or solid (mg/g) form. As a result initial processing steps might involve process volumes 100× larger than formulation steps. These distinctions are blurring now that antibodies and other biopharmaceuticals can reach 30 mg/mL in fermentation feed and early ion exchange or other purification steps achieve 100 mg/L. Formulation often involves combining protein or other biopharmaceutical with excipients such as polymers including Dextrans™, poly(ethylene glycol)s or Polysorbates™ (polyethoxylated sorbitan and laurate) and various commercially available copolymers or block copolymers of oxyethylene or oxypropylene such as Tergitols™ or Pluronics™. Excipients can be charged including use of other proteins (i.e. charged amphipathic biopolymers) such as albumin. Excipients stabilize the biopharmaceutical during storage, maintain high concentrations without inducing aggregation, and allowing for rapid dissolving and uptake in the body. Some polymeric or other excipients may also enhance not only the delivery but the pharmacological properties of drugs via for example adjuvant action. Given the above it is natural that any partition, precipitation or other unit operation method which localizes antibodies or other target proteins in solution, or insoluble complex, with biocompatible polymers should be of interest not only in regard to purification but also formulation, storage, delivery and efficacy of biopharmaceuticals. Especially as polymers such as those noted above are often found in antibody and other pharmacological formulations. One key point is that any commercially viable method must be able to handle complex feeds which include proteins or other targets at relatively high concentrations (e.g. >10 g/L), and process them without significant (i.e. >2×) dilution. The above considerations hold not only for recombinant protein, nucleic acid and other biopharmaceuticals but also for vaccines, and other biotherapeutics and bioparticles.

Vaccines, and especially viral vaccines pose a set of interesting processing challenges illustrated by the processing of influenza vaccines. Much flu vaccine is produced in eggs. This offers the interesting challenge of removing ovalbumin protein and other contaminants from the viral targets. This is often done via sucrose density gradient centrifugation. However modern processing is going more and more over to processing of viral vaccines in cells (typically MDCK or Vero kidney cell lines) grown either in suspension culture or adherent culture where the cells grow attached to colloidal carriers. In both cases the cultured cells are infected with virus, which propagate to the point where the cells either lyse naturally or are readily lysed by various chemical or physical treatment. In both cases the end results is a complex feed which contains various larger (>1 micron) particles, cell debris, intact virus (which is the target to be purified) and virus related debris such as cell membrane fragments containing viral proteins. Following use of centrifugal or other methods to remove cells and related debris, sucrose density gradients may be employed to separate the viral related fractions into intact and debris fractions. Such methods are of course decades old technology and there have been attempts to employ newer separation methods such as aqueous polymer two phase partitioning or column chromatography. Most work involving partitioning of viruses was done over ten years ago and has been reviewed by Lena Hammar (Lena Hammar, Concentration of Biomaterials: Virus Concentration and Viral Protein Isolation, Chapter 62, pp. 627-658, in Methods in Enzymology, Volume 228, Aqueous Two-Phase Systems, H. Walter and G. Johansson, Eds., Academic Press, New York, 1994) where she noted that "Extraction in aqueous polymer systems remains an attractive option when virus purification from large volumes is involved and in dealing with labile viruses". Hammar and related references provide many examples of partitioning of a wide variety of different viruses of medical significance. The labile nature of viruses generally dictate that two polymer (typically PEG and dextran) phase systems, which offer lower interfacial tensions than single polymer and high salt (e.g. PEG and sodium phosphate) systems were used. Naturally fractionation of virus using such systems suffers many of the same drawbacks which are related to processing antibodies or other macromolecular targets via partitioning. This includes cost of two polymers, and addition of a separate partitioning step to a process. Some vaccine processes recovery of viral product after centrifugal clarification followed by sucrose density gradient fractionation can be as low as 20%. An inexpensive partition system which offered as good or better recovery while replacing one or both of the clarification and density gradient steps is desirable, especially if it could be performed in disposable bag format, rather than in fixed line centrifuges. Commercial viability of partition processing of viral vaccines must also rest on new inexpensive systems which offer excellent selectivity. Such a goal is achieved in this application.

BRIEF DESCRIPTION OF THE INVENTION

The present invention relates to a process of enriching one target compound from a liquid, which process comprises at least one step of isolation performed by differentially partitioning between two aqueous phases. In the present invention the phases are formed by adding a single type of responsive, self-associating (i.e. clouding) hydrophilic polymer, and optionally some additional salts, to an aqueous biological solution (such as a fermentation sample or bioseparation process stream) under thermal and other conditions where the solution separates into a one polymer, two-phase system with one phase enriched in the polymer. The target compound is to be found in the phase not enriched in the polymer, while a significant though varying percentage of contaminants including cells or cell debris differentially partition to the phase interface or the polymer enriched phase. As such the process can be performed on fermentation broth or other complex biomass containing solutions to achieve a significant degree of clarification and purification in a manner which allows direct further processing of the target containing phase, via further standard separation operations such as chromatography.

The inventors have discovered conditions where commercial thermoresponsive polymers such as Breox can be added directly to unclarified fermentation broth with minor amounts (0.1M or less NaPhosphate) of added salt and, at the bioreactor culture temperature, effect formation of a two phase system consisting of a self associated polymer rich phase and a target containing aqueous phase. Several target proteins such as antibodies in unclarified CHO feed (broth), green fluorescent protein in *E. coli* broth, or antibody fragments have been shown to be almost completely recovered into the cell debris free upper phase. Host cell protein, nucleic acid particulate contaminants partition to varying degrees to the polymer rich phase or the phase interface. Due to its relatively low salt concentration the target containing phase can then be employed directly in commonly used downstream processing steps such as filtration or chromatography, where residual polymer will exhibit no negative impact on target purification, and be isolated from target in a manner requiring no unit operation addition or significant modification.

The systems is successful in handling concentrated cell containing solutions where target protein exceeds 10 g/L. The partition step can be performed in disposable or fixed bioreactors, or other containers, and in scales from milliliter to thousands of liters, and cost advantageously effect primary clarification, preliminary target purification, and some process volume reduction. It is amenable to polymer recycling or use with multiple extraction formats. It is suitable for use with a wide variety of complex biological solutions such as culture broth or even milk or plasma; as well as for high throughput process development or analysis, various kit formats, and various targets. In influenza virus vaccine production from cultured eukaryotic cells, the systems can effect clarification of cell debris and partitioning of protein under conditions which allow recovery of viral fraction of commercial interest. Thus the system could also be used in processing large number of viruses and other colloidal and nanometer to micrometer scale particles.

DETAILED DESCRIPTION OF THE INVENTION

Figure 1:
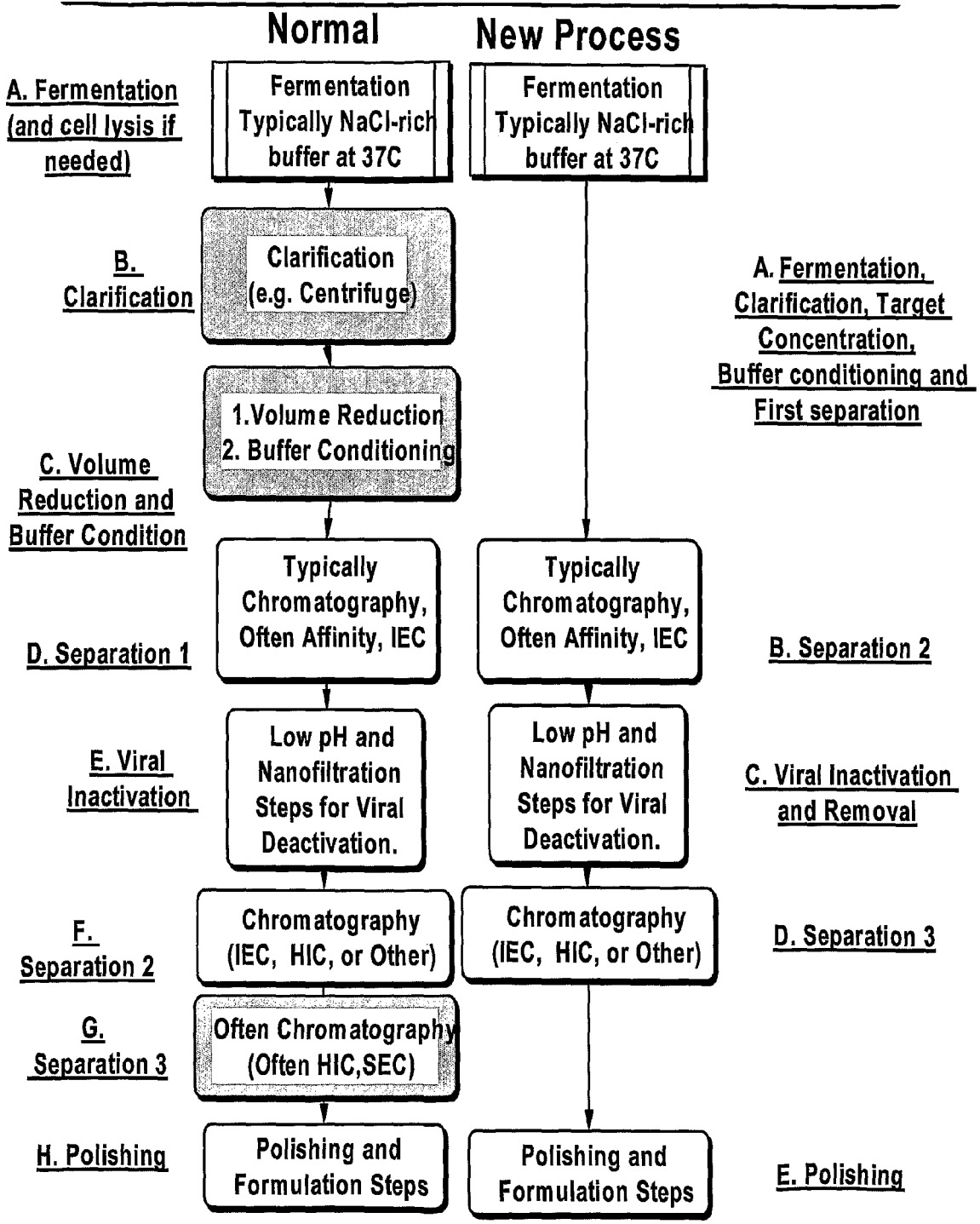
FIG. 1. Simplified process flow charts related to monoclonal antibody or similar recombinant protein being purified in processes with and without a partition step such as of the invention.

The present invention relates to advantageous uses of an aqueous polymer two phase system for the isolation of biomolecules or target compounds, which target compounds mean compounds as well as molecules and cells, i.e. any entity which it is desired to isolate from a liquid.

Thus, the invention relates to a process of isolating one or more biomolecules or target compounds from a liquid, which includes combining, in a container, a hydrophilic poly(ether), at least one salt and a liquid comprising the at least one biomolecule or target compound; gentle mixing of the liquid mixture obtained until at least two phases are formed; and, optionally, recovering the desired biomolecule or target compound from one of the phases.

The polymers used in the liquid mixture and multiphase system used in the present invention are aqueous in the sense that they form aqueous phases when combined with water. Further, as understood by the skilled person, in the present context the term liquid "mixture" refers merely to a combination of the herein-defined components. Under which conditions such liquid mixtures exist as one, two or more phases is deducible from phase diagrams. One advantage of the liquid mixtures of the invention is that they give rise to phases which, due to very low (typically <3% w/w) polymer concentration in the target containing phase appear less viscous, optically clearer and easier to further process than many commonly studied polymer-salt or two-polymer phase systems.

In an advantageous embodiment, the hydrophilic poly(ether) is a synthetic polymer comprising ethylene oxide units. In an advantageous embodiment, the ethylene oxide polymer is selected from the group consisting of water soluble poly(ether)s which includes poly(ethylene)glycol (PEG); ethylene oxide propylene oxide (EOPO) in either random copolymer form (e.g. Breox® or UCON polymers) or block polymers (e.g. Pluronic® polymers), ethoxy-containing polysaccharides and isopropylacrylamide modified polymers. As the skilled person in this field will realise, these polymers may include variously modified forms, such as. monomethoxy forms of PEGs. In an advantageous embodiment, the hydrophilic poly(ether) is EOPO. As is known by the skilled person, EOPO separates into two phases when above its cloud temperature (Tc) and is consequently regarded a thermoseparating polymer.

In one embodiment, the molecular weight the hydrophilic poly(ether) is in the range of 900-100,000 Da, such as 1000-20,000 Da. In one embodiment, the molecular weight is in the broad range of 400-1,000,000 Da which thermoresponsive polymers may be obtained in commercially.

Much is known about the phase separation of thermoresponsive polymers due to their use as surfactants, and other applications. Thus, the skilled person can easily decide suitable conditions such as pH and temperature at which a multiphase system, such as a two phase system, is formed from the present liquid mixture based on phase diagram data and optionally very simple routine experimentation. In one embodiment, the pH value of the present liquid mixture is close to neutral. The temperature may be in the range of 4-50° C., such as room temperature to about 40° C., for forming a two phase system suitable for bioprocessing. It is noted that some thermoseparating polymers such as polyethylene glycol have Tc values close to 100° C.

As the skilled person will understand, the present synthetic poly(ether) is chosen to be able to form an aqueous two phase system in the presence of enough salt (often 200 mM). If the target containing solution, such as culture broth, contains salts such as 0.15M NaCl it may only be necessary to add 50 to 100 mM NaPhosphate or other salt. In a similar manner if the target containing solution such as culture broth is already at or above Tc (e.g. 37° C.), little or no heating may be required to effect phase separation. The two-phase systems formed from the liquid mixture of the invention may contain other charged and noncharged groups, including polymer coupled affinity ligands.

Some advantages of the new one polymer two-phase system compared to classic polymer-polymer and polymer-salt two phase systems are shown in Table 1.

In a specific embodiment of the present system, the total salt concentration is in the range of 1-500 mM, such as in the range of 100-300 mM. As the skilled person will understand the amount of salt needed to form a two-phase system will be influenced by polymer MW, concentration and physical status.

In an advantageous embodiment, the salt is selected from the group consisting of NaCl, $Na_2PO_4$, $KPO_4$, $NaSO_4$, potassium citrate, $(NH_4)_2SO_4$, sodium citrate, sodium acetate and combinations thereof. Other salts, e.g. ammonium acetate, may also be used.

The total polymer concentration of the present liquid mixture can be optimised for each envisaged use. For example, it is well known that proteins and other macromolecules can be precipitated out of solution by addition of relatively high amounts of water soluble polymers. Therefore, if the system according to the invention is to be used in protein separation, too high a total polymer concentration would not allow for sufficient protein solubility to achieve a cost efficient separation. Thus, in one embodiment of the present liquid mixture, which is advantageous for the isolation of biomolecules and/or particles, the total polymer content constitutes about 4-20% (w/w) of the total system but following phase separation polymer concentration in one phase may typically be only 1 to 3% w/w with most of the polymer self-associated in the polymer-rich phase.

TABLE 1

Comparison of Main Operational Attributes of Classic Two Component, and New One Component Aqueous Polymer Phase System Partition as Unit Operations

| | Property | Classic 2 Polymer Biphase | 1 Polymer + Hi Salt Biphase | New 1 Polymer Biphase |
|---|---|---|---|---|
| 1 | Technically simple and robust operation. | + | + | + |
| 2 | Readily integrate target containing phase with follow on unit operations, and therefore with various new and existing processes. | + | − | + |
| 3 | Fast (kiloL/hr) processing. Handles future loads (>10 KL, >20% solids, >10 g/L target) without diluting and increasing process vol. | − | − | + |
| 4 | Affordable (<<10 Euro/L) without recycling of polymers and salts. Process Savings > Cost. | − | − | + |
| 5 | Target (e.g IgG) recovery >90% with little apparent target aggregation or alteration. | + | ? | + |

TABLE 1-continued

Comparison of Main Operational Attributes of Classic Two Component, and New One Component Aqueous Polymer Phase System Partition as Unit Operations

| Property | Classic 2 Polymer Biphase | 1 Polymer + Hi Salt Biphase | New 1 Polymer Biphase |
|---|---|---|---|
| 6  1° clarification w/o centrifugation. | + | + | + |
| 7  Target can be partitioned into phase which contains little (e.g. 1%) residual polymer. | − | − | + |
| 8  Some contaminant (HCP, DNA, virus removal) due to asymmetric partition. | + | + | + |
| 9  Inexpensive, nontoxic, reagents. Removed without adding extra downstream steps. | − | − | + |
| 10  Easily validated operation and process. | + | + | + |
| 11  Able to be optimized via HTPD, with ready modeling and scaling to process scales. | + | + | + |
| 12  Suits varied biological samples including fermentations, e.g. CHO cells or *E. coli*. | + | ? | + |

+ = yes, − = no, and ? = possibly, HTPD = high throughput process development, CHO = Chinese hamster ovary cells, HCP = host cell protein, KL = 1000 liter The phase systems themselves can be compounded and mixed according to their use and need. Relative low viscosity and interfacial tension of the phases and phase mixtures means that mixing can be accomplished in variety of standard approaches such as by magnetic stir bar stirring, disposable (WAVE™) bioreactor bag rocking back and forth, or normal mechanical stirring paddles in fixed reactors.

In one embodiment, the phase system contains a polyethylene glycol (PEG) polymer modified affinity ligand. Such polymers are excluded from the EOPO polymer rich phase as the EOPO self associates. Such PEG-affinity ligands may be used to enhance target transfer into the polymer-poor phase. Many known PEG-affinity ligands exist including some hydrophobic ligands which are commercial PEG-fatty acyl surfactants such as those of the Brij® and Mrij®series. In a specific embodiment, the multiphase system comprises one or more chromatography ligands. Such chromatography ligands may be used as a tool when applying the present liquid mixture to isolation of biomolecules or compounds, in which case the ligands may bind a certain target compound partition said target compound to the phase favoured by the ligands. In one embodiment, the ligands are affinity ligands, which are capable of binding target molecules by highly specific interactions of the "lock/key" type, such as between receptor and ligand, or antibody-antigen. Illustrative affinity ligands are e.g. Protein A or Protein A-based ligands. In an advantageous embodiment, the affinity ligands are modified to facilitate their partitioning to a specific phase. In another embodiment, modified affinity ligands are added to partition interacting targets into the polymer poor phase.

The biomolecule or target compound isolated in the present process may e.g. be a protein, peptide, nucleic acid, cell, virus, or any part, fragment or fusion product of anyone of the above. Thus, in one embodiment, the target compound is an antibody such as a monoclonal antibody, or a fragment or fusion product thereof. Illustrative antibody fragments are e.g. Fab fragments. In another embodiment, the target compound is a nucleic acid, such as DNA or RNA, e.g. a plasmid, genomic DNA, an aptamer or an oligonucleotide. In an additional embodiment, the target compound is a cell, such as a eukaryotic or a prokaryotic cell, for example an adult cell or a progenitor cell. Thus, in one embodiment of the present process, the biomolecule is an antibody, preferably a monoclonal antibody. In another embodiment, the target compound is a Fab fragment.

In one embodiment, the biomolecule or target compound is isolated from the polymer poor phase. In an advantageous embodiment, the polymer poor phase is the upper phase of the at least two phases.

In one aspect, the present invention is a multi-step process of isolating one or more biomolecules or target compounds, wherein the clarification of feed is performed using partitioning between the phases of a multiphase system comprising a hydrophilic poly(ether) and at least one salt, which clarification is followed by at least one capture step, such as affinity chromatography. Advantageously, the partitioning step also reduces the host cell protein (HCP) and other contaminant levels in the clarified target rich phase. The feed may be any liquid wherein a biomolecules or target compound has been produced, such as a fermentation broth or a biological fluid, including bacterial and eukaryotic cell fermentation cultures. If required, the process includes a step of lysing cells to release biomolecules or target compounds before the clarification in a two phase system according to the invention.

In an advantageous embodiment, the aqueous two phase system is formed in a container where fermentation was carried out, such as in a fermentation vessel.

In another advantageous embodiment, the target rich phase is the polymer poor phase which preferably is the upper phase of the at least two phases. In a fermentation vessel, or disposable container, the collection of the upper phase can be more conveniently achieved with removal of the lower phase and phase interface leaving the upper, target containing phase available for further processing.

In another embodiment the approximately 1 to 3% residual polymer in the phase not enriched in polymer may provide some protective effect to the target protein or other substance. For example the antifreeze and antioxidant effects of polyethers in solution are both well known. Residual polymer may therefore be of use both as excipient or to better promote efficacy of the agent being purified. In another embodiment any residual polymer in the phase containing the target may aid further downstream processing for example in terms of enhancing capture chromatography according to US2007213513 (GE Healthcare).

Thus in one embodiment, the novel aqueous two phase system provides a simple and effect clarification of the feed, as well as primary concentration (volume reduction) and purification (reduction in non-target concentration) of target compound or biomolecules. This can be performed over a broad liquid scale range, milliliter (gram) to thousand liter (metric ton) in various containers, such as plastic microtiter plates, plus fixed metal or disposable plastic fermentation vessels. Our results suggest that targets can be recovered at a very high level in an aqueous phase containing only residual (often 1%) of biocompatible polymer which does not negatively affect further downstream processing in normal manner or require significant modification of standard unit operations or related procedures.

As the above discussed process is effective for partitioning target compounds and biomolecules, in manner that does not dilute them, and does not require undue salt concentrations, or yield target compounds in exceedingly viscous solutions, such a process can be readily coupled in line with other commonly used separation steps, from stacked disk centrifugation to chromatography and filtration. Accordingly, the phase containing the target biomolecule or compound is further subjected to at least one step of liquid chromatography with minor or no modification.

One possible scheme showing how the new approach might be used is given in FIG. 1. On the left one sees a normal three chromatography step separation process which might be used, for example, in Mab purification. Following fermentation and, if needed, cell lysis the fermentation feed is centrifuged to remove cells and cell debris. It is then filtered and subjected to buffer change prior to applying to an affinity column. It is then eluted and subjected to low pH viral sterilisation and following another buffer change subjected to two more chromatographic steps such as ion exchange followed by another ion exchange or hydrophobic interaction chromatography. In some cases one of the above non-affinity steps might be replaced by a mixed mode chromatography step. On the right is one proposed workflow of this invention. One sees how a phase system is formed in the feed (gaining dual use of feed salts and temperature) rapidly effecting primary removal (clarification) of cells and cell debris, as well as some possible reduction (depending on phase system) in various contaminants such as nontarget host cell proteins (HCP), nucleic acid, endotoxin and virus. The target containing upper phase can be applied directly to an affinity column, though use of simple depth filtration should enhance column life. The process continues in normal fashion except that including a partition based purification step up stream may also reduce the number of other purification steps or allow such steps to be run in flow through rather than capture mode. Residual polyether polymers in the process stream are not expected to adversely affect chromatographic performance (e.g. US2007213513).

In one embodiment, the liquid chromatography comprises affinity chromatography such as binding to Protein A ligands. Protein A chromatography is a well known method, and is in this context understood to encompass adsorption to any resin which comprises recombinant or native Protein A; parts of Protein A or any other modified form of Protein A which has retained its selectivity towards antibodies. Commercially available Protein A resins include e.g. the MabSelect family (GE Healthcare). Other affinity methods include immobilised metal affinity chromatography (IMAC).

The chromatography step may be followed by one or more additional chromatography steps and optionally steps for virus removal. In one embodiment, the chromatography is followed by affinity chromatography, ion exchange or hydrophobic interaction chromatography (HIC). Anion exchangers, cation exchangers and HIC resins are well known and commercially available.

In another embodiment, the affinity chromatography is followed by multimodal ion exchange chromatography. Multimodal ion exchange is also well known, and utilises a ligand that comprises more than one functional group such as an ion exchanging group in close proximity to a hydrophobic group. Illustrative examples are Capto™ MMC and Capto™ Adhere (GE Healthcare).

In another embodiment the initial affinity chromatography step may be replaced by one or more target size exclusion steps or perhaps capture or flow through (chromatography or filtration or similar) steps related to ion exchange, hydrophobic interaction, or mixed mode interactions.

The poly(ether) polymer based one-polymer, two-phase systems is ideal for use in large scale bioprocessing operations involving Mabs, Fabs and other targets. They eliminate or reduce the need for centrifugation based clarification. Clarification and some preliminary purification and concentration may be effected in phases which can be directly applied, with optional filtration, to chromatography capture media.

The system offers significant advantages on cost (one polymer, low salt) and others (target solubility) that suggest it could be ideal for inserted between fermentation and capture chromatography to replace the need for using centrifugation or other active processes for clarification. Such partition appears generally applicable and can handle protein dense and viscous feeds. Of course the partition approach might also be used to enhance target recovery in processes using centrifugal or filtration based clarification.

In another aspect, the present invention is a method of isolating at least one antibody from a liquid, which method comprises a step of partitioning in a multiphase system comprising a synthetic hydrophilic poly(ether), and at least one salt.

In an advantageous embodiment of the present method, the antibody is a monoclonal antibody, which is recovered from the polymer poor phase of the system. Thus, in a specific embodiment, the multiphase system used to isolate the antibody such as a monoclonal antibody is an aqueous polymer two phase system comprising about 4-20% EOPO, with 100-500 mM salt present.

The present invention provides an advantageous method for separating an antibody such as a monoclonal antibody from a fermentation or other complex feed containing contaminants.

In one embodiment, the present method comprises forming the two phase system as described above, followed by removal of the phase which is rich in thermoseparating polymer, such as EOPO.

In another aspect, the present invention relates to the use of a liquid mixture or multiphase system as described above in the separation of at least one target compound, such as a biomolecule, cell or particle.

In another aspect the partitioning step is used to preliminarily clarify, and purify (subfractionate) feeds or other complex solutions related to processing of viruses or other nanometer to micro sized particles.

In another aspect the partitioning step of the present invention, encompassing adding one thermoseparating polymer to feed or other target containing solution may be repeated so as to further purify a certain target. Such repeated partitioning steps might be effected under exactly the same conditions or under different conditions. The latter might allow for sequential purification of certain protein or other fractions.

In another aspect, the present invention relates to a process where the phase forming polymer can be recovered in form of a self associated polymer rich phase and recycled.

In yet another aspect, the present invention is a kit for the isolation of at least one target compound, such as a monoclonal antibody, which kit contains a liquid mixture or multiphase system as described above. In an advantageous embodiment, the present kit comprises at least one polymer, which is a synthetic poly(ether), in aqueous solution or in dry form.

Other features and advantages of the invention will be apparent from the following examples and from the claims.

EXAMPLES

A. Examples Related to Cells, Antibodies and other Macromolecules

General Experimental
1.1 Materials
Chemicals

| | |
|---|---|
| Breox 50 A 1000 (equal copolymer ethylene oxide and propylene oxide (EOPO) | Mw 3 900 See below. |
| Polyoxyethylene 100 Stearate (Myrj59) | Mw 5 450 Sigma, Ref. P-3690 |
| Gammanorm (polyclonal IgG) (pI approx. 7) | Octapharma Batch C19A8601 |
| Bovine serum albumin (BSA) (approx. pI 5.6) | Sigma, A7638 |
| Myoglobin (approx. pI 7) | Sigma, M1882 |

All other chemicals used in this study were of Analytical grade and purchased from E. Merck, Darmstadt or Sigma Aldrich.
Unless noted EOPO polymer refers to Breox 50 A 1000 which is a random copolymer consisting of 50% ethylene oxide and 50% propylene oxide with a molecular mass (number average) of 3900 Daltons. It is FDA approved for some applications and was obtained from International Specialty Chemicals (Southampton, UK) which is now part of Cognis (www.cognis.com)
Monoclonal Antibodies and Fermentation Samples
Purified Monocloncal Antibodies (Mabs)
    The following two proprietary Mabs (Mab 01 and Mab 03) were used.
Mab 01
    Purified with Protein A and Anion Exchange Chromatography Concentrated 10× Produced in CHO cells and stored in glycerine phosphate pH 7.8 and 5.2 mS/cm. Concentration 4.4 mg/ml, MW estimate 150 kDa, pI estimate 9.
Mab 03
    Purified with Protein A and Anion Exchange Chromatography Concentrated 10× Produced in CHO cells and stored in phosphate buffered saline pH 5.8 and 16.2 mS/cm. Concentration 5.8 mg/ml, MW estimate 150 kDa, pI estimate 7.
Real Feed Samples
    Four 'real' unfiltered, unclarified Mab fermentation feeds were obtained from Chinese Hamster Ovary (CHO) cell based fermentations. They contain different Mabs and are named feed 1, 2, 3 and 4. Green Fluorescent Protein (GFP) was expressed in *E. coli*.
1.1 Methods
    Each aqueous two phase system (ATPS) solution was prepared directly in a 10 ml Sarstedt tube (unless otherwise stated) by mixing appropriate amounts/volumes of the stock solutions listed below. The final volume of each system was 5 ml. The mixtures were vortexed about 30 seconds and were then left for phase formation for about 15 min at 40° C. in a water bath.
Stock Solutions:
EOPO, 20% (w/w): Prepared by dissolving 10 g EOPO in 40 g MQ water.
EOPO, 40% (w/w): Prepared by dissolving 20 g EOPO in 30 g MQ water.
Myrj59 (8 μM): Prepared by dissolving 3.6 mg Myrj59 in 100 ml MQ water.
Myrj59 (400 μM): Prepared by dissolving 0.18 g Myrj59 in 100 ml MQ water.
NaP (Na-phospahte, 0.8M): Different pHs (pH 5, 6, 7, 8) were made by mixing 0.8 M $NaH_2PO_4$ and 0.8 M $Na_2HPO_4$.
NaCitrate (0.8 M): A stock solution of pH 7 was prepared by mixing 0.8 M $Na_3$Citate and 0.8 M Citric acid.
NaCl (5 M): Prepared by dissolving 14.6 g NaCl in 50 ml MQ water.

Example 1

Effect of Na Phosphate Concentration and pH on Formation of ATPS

Aqueous two-phase system (ATPS) based on one polymer (EOPO) were prepared directly in a 10 ml Sarstedt tube by mixing appropriate amounts/volumes of the stock solutions. The final volume of each system was 5 ml. The mixtures were vortexed about 30 seconds and were then heated to about 40° C. in a water bath for about 15 minutes for phase formation.

ATPS based on 8% EOPO, 150 mM NaCl and 50-200 mM NaPhosphate buffers at pH 4, 6, 7 and 8 were prepared. After incubation at 40° C. in a water bath for about 15 minutes two-phase systems formed at all the pH studied.

In another set of experiments different concentrations of NaPhosphate buffer at pH 7 were used to prepare ATPS of 8% EOPO containing 150 mM NaCl.

The results suggested that
(1) No two phase systems were formed when low concentration of Na phosphate (20 mM) was used. However, when the Na phosphate concentration was increased to 50 mM the two phase system was formed.
(2) A higher phase volume ratio (5.25) was obtained with the ATPS prepared with 50 mM Na phosphate compared with ratio volumes of 4 from the other systems prepared with 100-300 mM Na phosphate.

This suggests that it should be possible to develop EOPO based two phase systems whose salt concentrations are low enough that their tonicity (osmolarity) is suitable for the partitioning of live cells without their being lysed. This is important in applications where (1) one wishes to primarily use the isotonic buffer salts in growth media to form a two-phase system with added EOPO concentrate, and (2) to clarify a ferment involving target protein transported out of living cells and process the cells without their lysing and releasing host cell proteins (HCPs) and (3) situations such as (2) where the cells are to be kept in continuous culture or otherwise processed in intact form.

Because the Ucon® polymers are very similar to Breox EOPO, they could be used in the place of Breox EOPO (see below) with minor modification of temperature related to changes in Tc. Many other similar polymers exist including Pluronic polymers. Pluronic L-81 (10% EO & 90% PO, Mwt 2700) was tested and two phase systems were successfully formed at room temperature when the polymer concentration was 10-20% in water or phosphate buffer. This could be significant for use under circumstances where the operator wishes to cool a fermentation to room temperature (e.g. to hinder protease activity).

Example 2

Effect on ATPS Formation and Protein Phase Partition of Antibody Concentration, or Use of GFP Containing Lysed *E. coli* Cell Paste ATPS based on one polymer (EOPO) were prepared according to description in Example 1. Table 2 shows four systems at different conditions where polycloanl IgG Gammanorm, or recombinant green fluorescent protein (GFP) containing lysed *E. coli* cell paste samples were tested.

TABLE 2

Phase Partition of Polyclonal Plasma IgG and GFP from *E. coli*.

| | EOPO % (w/w) | NaP mM | pH | NaCl mM | Phase form | Vol. ratio (U/B) | Sample | K A280 | C/Co = (K/K + 1) * 100% |
|---|---|---|---|---|---|---|---|---|---|
| 1 | 10 | 200 | 7 | 200 | Yes | 3.8/1.2 | 25 mg Gnorm | 9.3 | 90 |
| 2 | 10 | 20 | 7 | 200 | No | — | 25 mg Gnorm | — | — |
| 3 | 8 | 200 | 7 | 150 | Yes | 4/1 | 25 mg Gnorm | >500 | 100 |
| 4 | 8 | 200 | 7 | 150 | Yes | 4/1 | 200 mg GFP | >500 | 100 |

K = $C_{A280}$ upper phase/$C_{A280}$ lower phase. Gnorm = Gammanorm IgG concentrate at 165 mg/ml (Octafarma) so 25 mg relates to 152 microliters. NaP = NaPhosphate pH 7. GFP was in form of lysed *E. coli* cell paste.

The results indicate that:
(1) Under the conditions studied no two phase system formed when low concentration of Na phosphate (20 mM) was used. However, when the Na phosphate concentration was 200 mM, a two phase system was formed.
(2) 90-100% of total absorption from Gammanorm polyconal human antibody were obtained in the upper, polymer-poor phase with 8%-10% w/w EOPO systems.
(3) All the GFP activity, measured at 490 nm, was found in the upper phase in system 4. The *E. coli* cell debris partitioned to the interface at unit gravity (g). When the test tube was centrifuged at 3000×g for 5 minutes all the cell debris sedimented to the tube bottom without any disturbances in the separated phases.

The effect of concentration of EOPO on phase volume ratio, and target recovery was studied. Systems were prepared with 5 mg Gammanorm, 5 to 14% Breox EOPO polymer, and 150 mM NaCl plus 200 mM NaPhosphate buffer, pH 7, of a final volume of 5 ml. At 40° C. phase volume ratios decreased inversely with EOPO concentration, with a ratio of 11.5 at 5% EOPO and a volume ratio of 2.33 at 14% EOPO. After phase formations the phases were separated and absorbance of each phase was monitored at 280 nm by spectrophotometer. The partition coefficient (K) and the % concentration of each protein in the upper phase (C/o) were calculated. All the systems showed high K values (>200) and 100% target recovery. This result is of practical significance as Breox and related polymers are relatively inexpensive so moving from a 6% to 12% EOPO system may be warranted if one is able to effect a significant reduction in the volume of fluid the target protein is recovered in, and effect target concentration early in a process.

To investigate the solubility of proteins in the EOPO-based ATP systems a series of experiments were performed using different amount of Gammanorm in 5 ml ATPS system (8% EOPO, 200 mM NaPhosphate, pH 7.4 and 150 mM NaCl). After phase formation the phases were separated and absorbance of each phase was monitored at 280 nm by spectrophotometer. The partition coefficient (K) of each protein in the upper phase was high (>200). The EOPO system under these conditions resulted in virtually 100% Gammanorm recovery. In another set of experiments with a 20% EOPO system, the capacity reaches 20 g/L under the same salt conditions giving >97% recovery. The results suggest that the EOPO system has a high capacity. This compares very favorably to both PEG/salt (approx. 1 g/L) and PEG/dextran (approx. 5 g/L) systems.

In order to be generally useful, the approach should work with cell culture media. We investigated if cell culture media could affect the formation of phases in EOPO-ATPS. Cell culture media (2.6 ml) were tested in 5 ml ATPS of 8% EOPO, 150 mM NaCl and 200 mM NaPhosphate. The results show that two phase systems were formed with all the cell culture media tested (Ex-cell CA CHO-3 Sigma 126K8042; BD CHO ref. 220229; Power CHO-1-CP Lonza 070920 and CA OPTI CHO ref 12681-011-(Invitrogen)). This is in addition to successful studies done with *E coli* broth/paste and with adding EOPO plus salts directly to protein containing solutions. However to speed processing it may be better to add concentrated stock solutions rather than dry powders (see below).

Example 3

Citrate Based EOPO One Polymer ATPS

Phosphate salts are suitable for phase system formation with Breox polymer in part as they form systems at relatively low concentration of salts (e.g. one tenth that of some PEG and salt two phase systems) and also because the systems formed appear to offer good target protein recovery and some selectivity as regards to non-target proteins. However phosphate salts are expensive to purchase and also expensive to dispose of By contrast citrate salts are less expensive and more ecologically friendly. NaCitrate buffer was tested here in preparation of new systems. Different concentrations of NaCitrate buffer, pH 7.0 at different temperatures as shown in Table 3 were used for preparation of systems containing 8% EOPO and 150 mM NaCl.

The result showed that:

Two phase systems can be formed with NaCitrate concentrations of 50-200 mM at a temperature of about 40° C.

Two phase systems can be formed with NaCitrate concentrations of above 250 mM at RT but with phase inversion reversed phase order (the polymer phase will be in the upper phase and the water phase in the bottom). The recovery of IgG in the water phase in such system was about 96%.

Lower phase ratio was obtained with systems prepared with NaCitrate concentrations of above 250 mM at RT compared with systems prepared at 40° C. and lower NaCitrate concentrations.

This proved that suitable EOPO systems could be generated using NaCitrate as one of the dominant salts—although some phosphate might be added to enhance buffer capacity at higher pH. The phase inversion noted has been reported previously (M. Pereira et al. Biochemical Engineering Journal 15 (2003) 131-138.) where the authors looked at partition of polygalacturonase (not Mab) in centrifuged fermentation sample supernatants with the Ucon-(NH4)2SO4 system at 30 and 40° C.

TABLE 3

Citrate based EOPO ATPS formation at different salt concentrations and temperatures.

| [Citrate] mM | T ° C. | Volume Upper (ml) | Volume Bottom (ml) | Volume Ratio |
|---|---|---|---|---|
| 50 | 40 | 4.25 | 0.75 | 5.6 |
| 100 | 40 | 4.15 | 0.85 | 4.9 |
| 200 | 40 | 4.15 | 0.85 | 4.9 |
| 300 | 40 | Turbid one phase | | |
| 200 | RT | One phase, clear | | |
| 250 | RT | 1.3 | 3.7 | 0.35 |
| | | *C/Co IgG = 4.1% | *C/Co IgG = 96% | |
| 300 | RT | 1.2 | 3.8 | 0.31 |

*IgG recovery calculated as C/Co × 100%

The effect of the concentration of NaCl in phase formation in citrate based EOPO ATP systems was evaluated at 40° C. and RT using 100-250 mM NaCitrate buffers. The result shows that NaCl has little effect on the formation of phases at 40° C. when 100-200 mM NaCitrate buffer was used. However, a concentration of at least 150 mM NaCl was required for phase formation at RT when 250 mM NaCitrate buffer was used. The effect of pH variation was tested with two different unclarified Mab real process feeds (2 and 3) in 8% EOPO based systems. Fractions from the upper phases were analyzed for Mab content by protein A chromatographic analyses which suggested Mab recoveries of greater than 98% using 100 mM NaCitrate and 150 mM NaCl at pH 7 to 8. Naturally the presence of other salts could affect the above results.

Example 4

HCP Partition in EOPO ATPS

Effect of pH and Hydrophobic Affinity Ligand:

In these experiments crude Mab feed 1 was partitioned in 5 ml system of 8% EOPO, 150 mM NaCl and 200 mM NaPhosphate, pH 6 and 8 or pH 8 containing 8 µM Myrj 59 surfactant (added to act as a PEG-alkyl hydrophobic affinity ligand). After incubation at 40° C. in a water bath for about 15 minutes the phases were separated and analyzed for the content of HCP (Table 4). The results suggest that better reduction of HCP may be obtained with buffers at higher pH (pH 8).

TABLE 4

Reduction of HCP as a function of pH and Myrj 59.

| | Sample or Phase | HCP (ng/ml*) | Phase vol. (ml) | Total ng HCP | Reduction HCP % | Mass balance HCP |
|---|---|---|---|---|---|---|
| | Control Mab feed 1 | 12569 | 2.6 | 32679 | | 100 |
| pH 6 | Upper phase | 6781 | 4.0 | 27124 | 17 | 83 |
| | Bottom phase | 658 | 1.0 | 658 | | 2 |
| pH 8 | Upper phase | 4494 | 4.0 | 17976 | 45 | 55 |
| | Bottom phase | 11975 | 1.0 | 11975 | | 37 |
| pH 8, 8 µM Myrj 59 | Upper phase | 4022 | 4.0 | 16088 | 51 | 49 |
| | Bottom phase | 13383 | 1.0 | 13383 | | 41 |

In the study there is a dramatic decrease in HCP upper partition (i.e. increase in lower phase partition) from pH 6 to 8—in terms of HCP concentration. The hydrophobic affinity ligand had only a small effect at pH 8, which may be due to the HCP entities analysed being relatively nonhydrophobic proteins.

Effect of pH on HCP Partition in Nacitrate Based EOPO ATPS:

HCP data for crude feed and ATPS treated Mab feed was measured. The results (see Table 5) suggest:

HCP reduction of 13 to 23% occurred.

Reduction of HCP increases with increased pH of the buffer.

Reduction of HCP increases with increased polymer concentration

These results are in keeping with the concept that the system is behaving like many other systems as regards hydrophobic and basic proteins, such as many antibodies, favoring the polymer-poor phase while some component of the HCP mixture (which typically contains several different acidic and negatively charged proteins) partition to a greater degree into the polymer-rich phase. Protein molecular weight (and hydrophobicity) may also play a role.

TABLE 5

Reduction of HCP as function of pH and polymer concentrations.

| Sample or System | pH | Mab | Phase | HCP* (ng/ml) | Phase vol. (ml) | Total HCP (ng) | HCP % Reduction |
|---|---|---|---|---|---|---|---|
| Feed 2 | | 2 | | 17158 | 2.29 | 39292 | 0 |
| Feed 3 | | 3 | | 5873 | 2.29 | 13449 | 0 |
| 8% EOPO, 100 mM Na3Cit. pH 8.3, 50 mM NaP pH 8, 150 mM NaCl | 8.1 | 2 | Upper | 8049 | 4.15 | 33403 | 15 |
| 8% EOPO, 100 mM Na3Cit. pH 8.3, 50 mM NaP pH 8, 150 mM NaCl | 8.1 | 3 | Upper | 2500 | 4.15 | 10375 | 23 |
| 8% EOPO, 100 mM Na3Cit. pH 7, 150 mM NaCl | 7.0 | 2 | Upper | | 4.1 | 33989 | 13 |
| 8% EOPO, 100 mM Na3Cit. pH 7, 150 mM NaCl | 7.0 | 3 | Upper | | 4.1 | 10894 | 19 |
| 12% EOPO, 100 mM Na3Cit. pH 7, 150 mM NaCl | 7.0 | 2 | Upper | | 3.6 | 30470 | 22 |
| 12% EOPO, 100 mM Na3Cit. pH 7.4, 150 mM NaCl | 7.0 | 2 | Upper | | 3.6 | 31105 | 21 |

*HCP determined from commercial ELISA test against standard curve.

Example 5

Concentration of Mab from Crude Feed

An approx. 10 ml ATPS based on 8% EOPO and 200 mM NaPhosphate buffer, pH 7.4 was prepared from 0.8 g of 100% EOPO polymer, solid phosphate salts (87 mg $NaH_2PO_4$ 245 mg $Na_2HPO_4$) and 9.2 ml of Mab feed 2. After mixing and incubation at 40° C. in a water bath for about 15 minutes a two phase system was formed. The total volume of the phases was 9.5 ml consisting of 7.7 ml water-rich upper phase and 1.8 ml polymer-rich bottom phase—to give a phase volume ratio of 4.27. This volume ratio is lower than a volume ratio from a system prepared using a 40% EOPO solution with 0.8 M NaPhosphate buffer which was 5.25. Thus, the Mab feed can be concentrated 16% with ATPS prepared from concentrated EOPO polymer and solid phosphate salts.

Earlier results indicate that phase volume ratios change inversely with EOPO polymer concentration. It was noted that moving from 8% to 12% Breox concentration may reduce target containing phase volume without affecting recovery. We investigated the recovery of Mab in ATPS of 12% EOPO polymer with different salt types (phosphate and citrate) and salt concentrations using Mab feed 2. Mab recovery in the water-rich phases was measured using protein A chromatographic analysis. The results show:

Recoveries of about 100% for both Mab feed samples when the system contain 100 mM NaCitrate and 150 mM NaCl at pH range of 7 to 8.

Smaller volumes of the water phases (3.5-3.6 ml) were obtained compared with systems based on 8% EOPO (4.0-4.1 ml). This means that higher concentration of Mab could be obtained when concentration of EOPO is increased.

We also tested different salt conditions at a polymer concentration of 20% EOPO. The results show that using 100 mM NaPhosphate with or without 150 mM NaCl the Mab containing water phase can be concentrated by 19 and 28%, respectively.

Example 6

Figure 2:
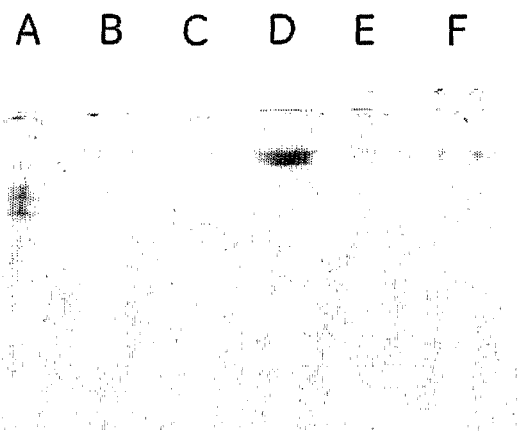
FIG. 2. SDS polyacrylamide electrophoresis gel demonstrating how partition step as per the invention can reduce nontarget protein in various recombinant fermentation feeds. A. MW standards, B. crude Mab feed 1, C. Upper phase 0.2M NaP system with Mab feed 1, D. crude Mab feed 2, E. Upper phase 0.2M NaP system with Mab feed 2, F. Upper phase 0.1M NaCitrate system with Mab feed 2. The major band in lanes B to F relates to monoclonal antibody.

Purification of Mab from Crude Feed Using Phosphate and Citrate Buffer Systems In this set of experiments 10 ml EOPO-ATPS based on 8% EOPO, 150 mM NaCl and different concentrations of NaPhosphate or NaCitrate buffers (and containing 2.6 ml of crude Mab feeds 1 or 2) was prepared. The 250 mM NaCitrate phase reversed system was kept at RT. The other systems were incubated at 40° C. in a water bath for about 15 minutes, to allow the phases to be separated. The purity of phases from some systems was analyzed by SDS page electrophoresis (gel gradient 8 to 25%) (FIG. 2). HCP data for crude and the recovered Mab after ATPS experiments are presented in Tables 6. From the results obtained it can be concluded that:

Mab was partially purified by ATPS with both NaPhosphate or NaCitrate buffer systems (see FIG. 2).

Reduction of more than 20% of HCP can be obtained by ATPS based on 200 mM NaPhosphate system and about 30% achieved with 250 mM NaCitrate buffer system (see Table 6).

Smaller volume of the water phase was obtained with the 250 mM NaCitrate buffer system compared with NaPhosphate buffer systems (6.5 ml to be compared with 8.2 ml, see Table 6). This means a higher concentration of the Mab in the NaCitrate system upper phase.

TABLE 6

Reduction of HCP as function of concentration and buffer type.

| Sample or System[+] | Phase | HCP[++] (ng/ml) | Phase volume (ml) | Total HCP (ng) | HCP Reduction % |
|---|---|---|---|---|---|
| Crude Feed 2 | | 16956 | 5.2 | 88171 | 0% |
| 200 mM NaP, pH 7.4 | Upper | 8559 | 8.2 | 70184 | 20.4% |
| 200 mM NaP, pH 7.4 Clarified feed | Upper | 8950 | 8.2 | 73390 | 16.8% |
| 100 mM NaCit., pH 7 | Upper | 10035 | 8.2 | 82287 | 6.7% |
| 250 mM NaCit, pH 7* | Bottom* | 9576 | 6.5 | 62244 | 29.4% |

[+]Systems were 10 ml and contained 8% w/w Breox, 150 mM NaCl, and crude Mab feed 2. One system contained clarified feed.
[++]UHCP determined by commercial enzyme linked immunoassay.
*= phase inversion (water rich bottom phase),
**= concentration effect.

One can again see ability of the phase systems to reduce HCP. In these studies it was assumed that the HCP went to the lower phase or to the phase interface. In the latter case it might have been associated with cell debris.

Example 7

Further Characterizations of the ATPS Systems

Conductivity of Water Phase:

In order to examine their suitability for follow on separation steps such as affinity or other capture chromatography the conductivity of the water phases was determined using 5 ml ATPS prepared from 8% EOPO, 150 mM NaCl, at different buffer concentrations (NaPhosphate or Na Citrate) and with or without (2.6 ml) crude Mab feed. The results show that the conductivities of the water rich (polymer-poor) target containing phases were about 30-40 mS/cm. We demonstrate below that the pretreated Mab with ATPS, which has a conductivity of about 35, could be applied directly on a MabSelect Sure (protein A related) affinity column for further purification. We propose that these solutions are also suitable for hydrophobic interaction chromatography, size exclusion chromatography, and some forms of mixed mode chromatography (or capture filtration). They may also be suitable for some forms of target flow through ion exchange or target capture ion exchange. Some dilution may be required if the sample is to be applied directly to an ion exchange column. However it has recently been shown that if a target protein such as Mab or Fab is highly charged it may be possible to achieve good binding at even 25 mS/cm (e.g. C. Harinarayan et al., Biotechnology and Bioengineering, 95 (2006) 775-787).

Analysis of Polymer Content in Two Phases:

Content of EOPO polymer in the water and polymer phases prepared from 8% EOPO, 150 mM NaCl and 200 mM NaP or NaCitrate buffers were analyzed by total carbon content (TOC) method. The results show that the content of EOPO polymer in the water phases was only about 1% (w/w). While the content was about 40% (w/w) in the polymer enriched phases. The result compares favorably with literature values for 10% (w/w) Breox 50A 1000 and water two-phase systems (Cunha et al. Journal of Chromatography B, 711 (1998) 53-60) where temperature needed to be raised to 60 degree C. to effect phase separation to yield systems with phase volume ratio of 8 and with top and bottom phase polymer concentrations of approximately 3% and 60% respectively. Thus in the current systems the polymer content in the target containing phase (to be loaded directly onto a column following filtration) is one third of Cunha et al.; most probably due to inclusion of phosphate or citrate salts at 200 mM. Further more a lower phase with 40% EOPO may be expected to have capacity for nontarget proteins to partition into to a greater extent than a system with 60% EOPO (w/w).

Separation of Mab Sample with 14% Microaggregate:

A Mab sample artificially enriched in self associated antibody (multimer aggregates) was subjected to partitioning in an 8% EOPO, 150 mM NaCl, 200 mM NaPhosphate, pH 7. Results suggest that there was no reduction or increase in aggregate concentration. This is perhaps not surprising given that the surface features of Mabs which provide for high partition would still be present on the aggregate surfaces. Similar results are expected for Mab dimmers. Thus partitioning should, ideally, be paired with selective, multi-plate separation method such as MabSelect affinity chromatography or Adhere multimodal chromatography. Partition should remove some larger aggregates once they reach a size to be held by phase interfacial tension.

Example 8

Purification of Mab Using ATPS and Protein a Column

Figure 3:
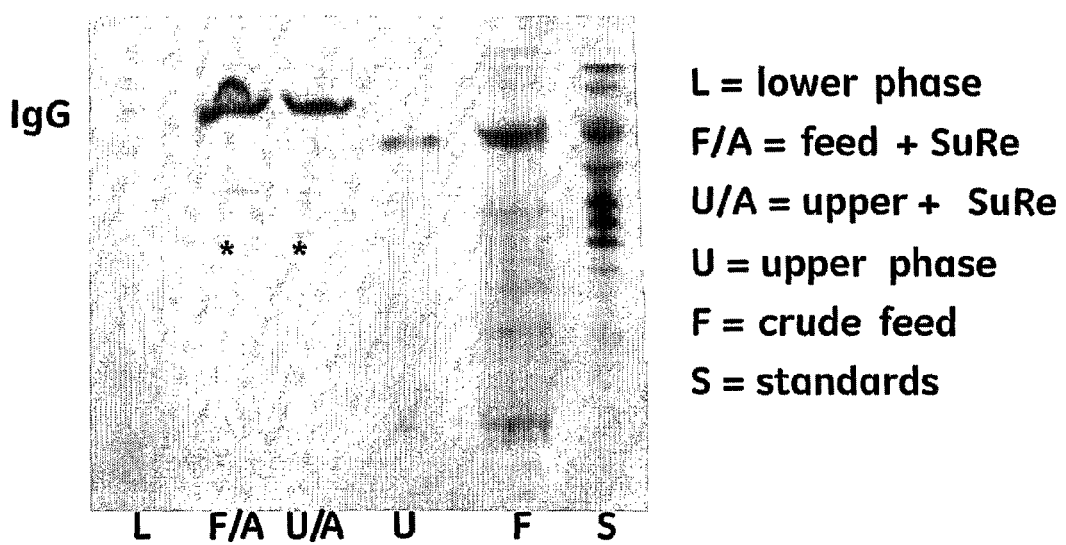
FIG. 3. Nonreduced SDS polyacrylamide electrophoresis gel (gel gradient 8 to 25%) demonstrating how partition step as per the invention can reduce nontarget protein in recombinant monoclonal antibody (Mab) fermentation (feed 2), and Mab in the upper phase can be loaded directly onto an affinity (MabSelectSure) column.

Crude Mab feed 1 (2.6 ml Mab) was subjected to treatment with (8% EOPO, 200 mM NaPhosphate, pH 7, 150 mM NaCl) system as described above. A 2 ml fraction from the upper phase was collected and applied on a HiTrap MabSelect Sure column for further purification. The applied sample had a conductivity of about 35 mS/cm. The column was pre-equilibrated with phosphate buffered saline (PBS) pH 7.4 and eluted with 60 mM Na-citrate buffer, pH 3.4. As a control, similar amount of crude Mab feed 1 without EOPO-ATPS but centrifuged and filtered (conductivity 12 mS/cm) was purified on the same column. The purity of the eluted fractions was analyzed by SDS page electrophoresis. Protein recovery and HCP data (from commercial ELISA) for crude and recovered Mab after ATPS and protein A chromatography experiments are presented in Tables 7 and 8. The results from these experiments suggest:

Mab was partially purified by ATPS with a recovery of 100% (FIG. 3, Table 7).

Figure 4:
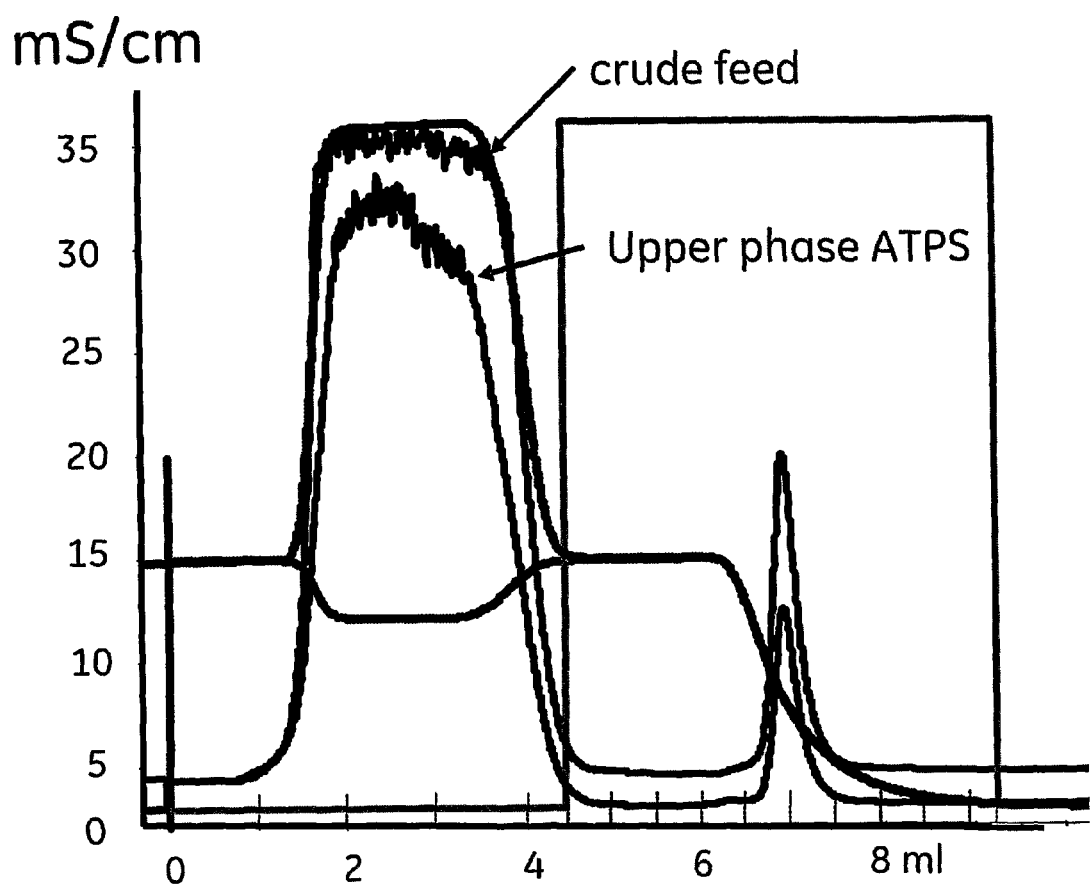
FIG. 4. Direct application of Mab containing phase to Protein A based MabSelect™ Sure affinity column. Crude feed sample was also run afterwards as a control. Note that while crude feed can be put onto a Protein A based affinity column this is not typically done as it leads to fouling of the column.

ATPS pretreated Mab sample can be applied directly onto MabSelect (FIG. 4).

Reduction of more than by 20% of HCP may be obtained by ATPS (with the studied feed and ATPS system) (see Table 8).

The shift in relative antibody band position between samples from ATPS and Sure processing is believed to be due to difference in (eluted) sample pH and conductivity (i.e. lower pH of Sure eluted samples), as well as presence of residual polymer in the ATPS sample. The diffuse nonbanding noted in the lower, polymer-rich, phase sample is believed to be due to host cell proteins partitioning into that phase interacting with polymer in that phase.

The recoveries from the protein A column are in the 60 to 70% range for this sample for both ATPS and feed samples. This is relatively low for protein A (typically 100% is normal) however some types of Mabs can show such results. Nevertheless ATPS partitioning yielded 100% recovery and did not alter performance of the column in comparison to Mab feed sample.

TABLE 7

Mab recoveries during different steps calculated from Mab Sure analysis data.

| Samples | Step | Mab (µg/ml) | Volume Loaded/ collected (ml) | Total µg Mab | Recovery % |
|---|---|---|---|---|---|
| Mab feed 1 | Before ATPS | 297 | (Loaded) 2.6 | 772 | |
| Mab in Upper phase-ATPS | After ATPS | 190 | (Recovered) 4.1 | 779 | 101 |
| Mab feed 1 | Before PrA | 297 | (Loaded) 2 | 594 | |
|  | After PrA | 375 | (Recovered) 1 | 375 | 63 |
| Mab in Upper phase-ATPS | Before PrA | 190 | (Loaded) 2 | 380 | |
|  | After PrA | 252 | (Recovered) 1 | 252 | 66 |

TABLE 8

Reduction of HCP during different steps.

| Samples |  | HCP (ng/ml) | Phase volume (ml) | Total ng HCP | Reduction HCP % |
|---|---|---|---|---|---|
| Mab feed 1 | Before PrA | 12011 | 2.6 (2 ml loaded on PrA) | 31228 (24022) | |
|  | After PrA | 53 | 1 ml fraction from PrA | 53 | 100 |
| Upper phase-ATPS | Before PrA | 5909 | 4.1 (2 ml loaded on PrA) | 24226 (11818) | 22 |
|  | After PrA | 53 | 1 ml fraction from PrA | 53 | 100 |

The ATPS step reduces the load of HCP applied to the column (Table 8), but did not affect the reduction following protein A chromatography. However reduction of HCP load by 22% (in this case) could benefit process in terms of reduced nonspecific fouling and increased column life.

Example 9

Purification of Mab Using ATPS and Capto MMC Column

The purpose here was to verify that the water-rich, target containing phase from the ATPS was compatible with subsequent chromatographic step involving multimodal cation exchanger Capto MMC. Real Mab feed 1 unclarified feed pH 7 was used. The approx. pI of the Mab was 6.5 and its concentration was at 0.4 mg/ml. The MMC was loaded with the water-rich target containing phase following partitioning of thermo induced phases. As a control, feed stock clarified by centrifugation was used. The composition for the ATPS systems was: 8% EOPO, 200 mM phosphate pH 7.4, 150 mM NaCl. In both cases load solution pH was adjusted to 5 prior to chromatography.

The Capto MMC media was packed in Tricorn 5/100, bed height of approx. 10 cm and a total volume of approx. 2 ml. Sample was 1 ml of target containing phase (not subjected to centrifugation) or clarified feed. The flow was 1 ml/min (300 cm/h) for all of the runs. The mAb was eluted by a pH-gradient. Fraction volume was 2 ml. Buffer A was 50 mM HAcetate pH 4.75 and Buffer B was 50 mM TrisHCl pH 9. Analysis was via gel filtration using a Superdex 200 5/150 GL column run with PBS at 0.3 ml/min.

Figure 5:
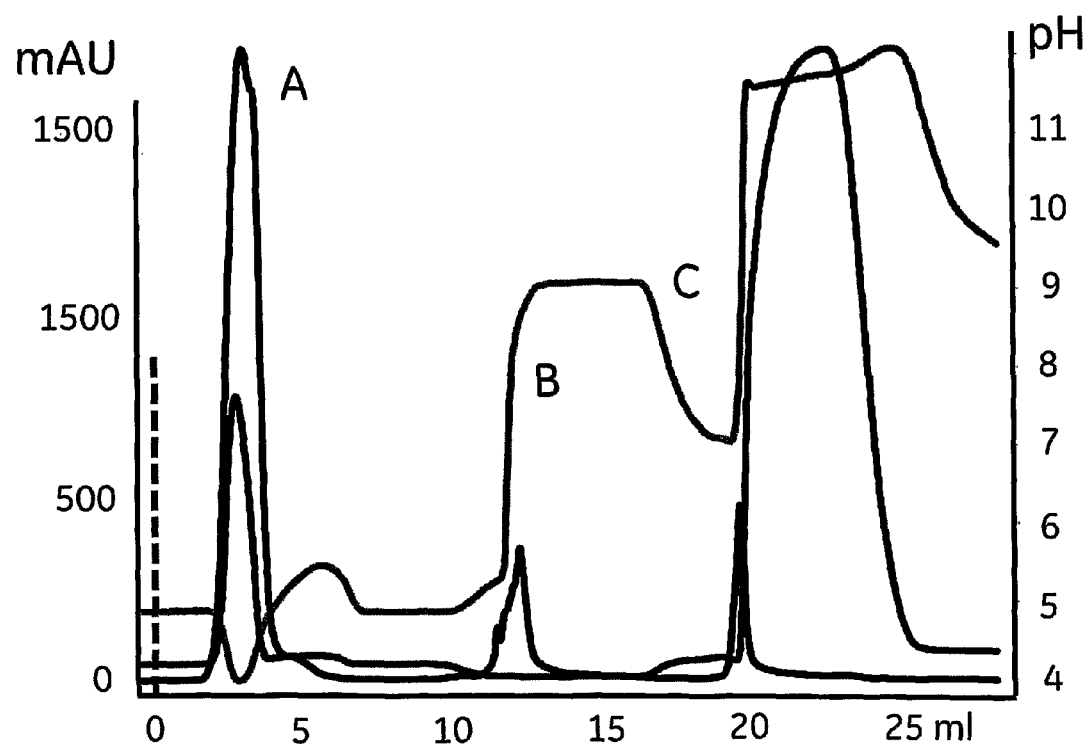
FIG. 5. Capto™ MMC multimodal chromatography of Mab first processed by partition in one polymer thermoseparated aqueous phase system per the invention. A. Flow through, B Eluate, C CIP.
Figure 6:
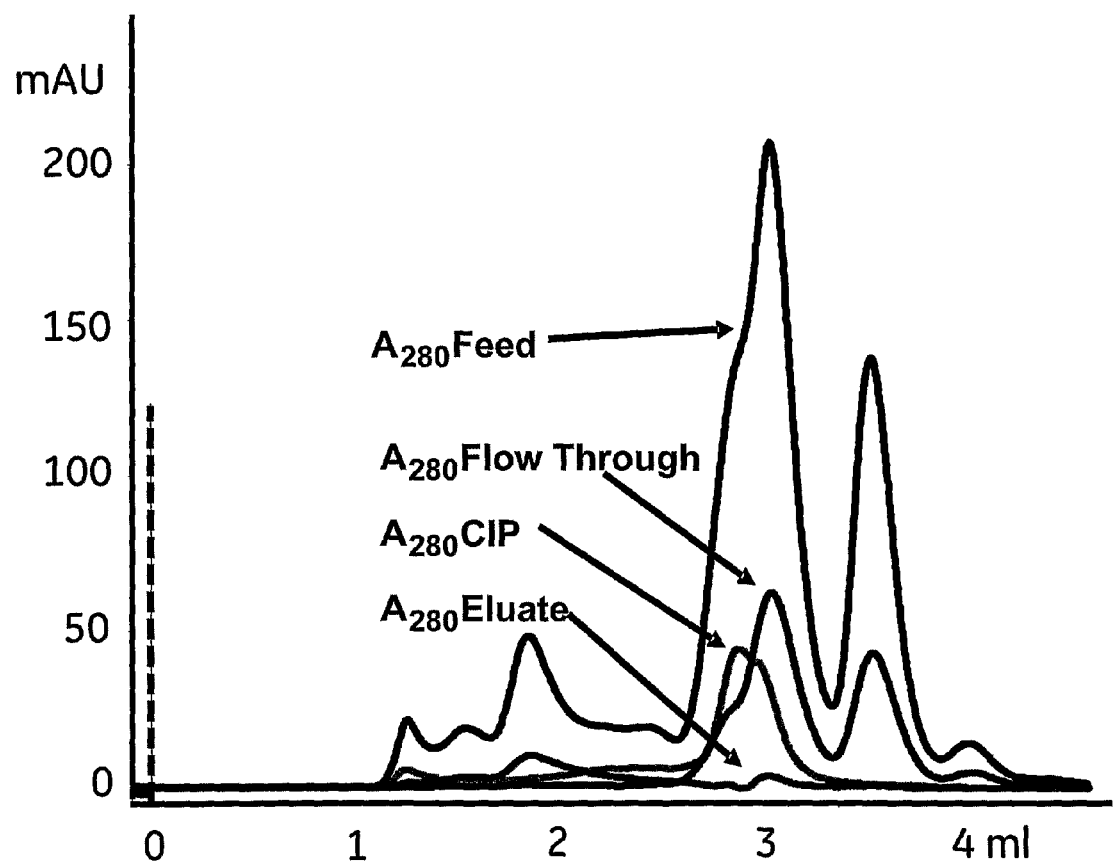
FIG. 6. Size exclusion chromatographic analysis on Superdex of elution and other fractions from the affinity chromatography in FIG. 5. Different curves corresponds to peaks A, B and C of FIG. 5 according to Flow Through, Eluate and Cleaning in place (CIP). Feed was also included. From left to right peaks represent proteins of decreasing MW. Feed and elutate are the only samples with appreciable antibody.

Initial experiments showed a rather distorted adsorption peak with analysis showing leakage of the mAb in the flow through. In addition some contaminants were detected in the eluate pool. We therefore diluted the feed sample by half to about 0.2 mg/ml Mab. The diluted sample was subjected to ATPS and the Capto MMC separation procedures and analyzed by gel filtration. The analysis showed good binding of the mAb to the Capto MMC medium since there was no leakage of mAb in the flow through (FIGS. 5 and 6).

Capto MMC is promoted as "high salt chromatography resin". These results show that Capto MMC could bind the tested mAb at conductivities related to undiluted target containing upper phase. An increase in pH to a point close or above the pI of the protein is the most efficient way to elute a bound protein. The recovery was 60-70% similar to the Mab-Select results. Reduction of HCP is about 90% similar to the feed result but lower than MabSelect.

Example 10

Scale Up Purification of Mab Using ATPS and Protein A Column

Here we show that partitioning according the invention does not interfere with mAbs in such a way that the formation of aggregate increases, the recovery is reduced or that the recovery and purity for the Protein A step is decreased. Thus the ATPS could act as a combined clarification and separation step and reduce the content of larger particles or aggregates that might lead to fouling of the Protein A column. By forming the ATPS directly in the fermentation vessel (or in vessel ferment is transferred to) partition can be part of the same unit operation without any loss of time. As a second step the mAb containing fraction (water-rich phase) was further purified using MabSelect Sure, in manner similar to that noted above.

The starting material was Mab containing CHO-cell fermentation feed 2 clarified by centrifugation. Clarified feed was used due to make it easier to follow phase separation kinetics. Mab concentration was approx. 0.4 g/l. The feed sample contained 15-20% (by A280) antibody dimers and aggregates judged by gel filtration.

Aqueous two phase systems were prepared directly in 1 liter glass cylinders by mixing appropriate amounts/volumes of the stock solutions of 40% (w/w) EOPO polymer and 0.8 M buffer solutions except for system 5 where 100% EOPO polymer and appropriate amounts of solid phosphate salt were used. The final volume of each system was adjusted to 800 ml by addition of the feed. Each system was mixed and was then incubated in the climate cabin at 40° C. except for system 3 which was kept at room temperature. After formation of the phases the time for phase formation, volume of each phase and phase volume ratio were recorded (see Table 9). The mAb containing water-rich phase from each system was then removed for further purification.

Table 9 Shows data from the various two-phase systems. Some of the boxes contain two values. This is due to the size of the intermediate phase. The inter phase can be collected in several ways. In system 5 the salts were added as solid crystals to the final concentration.

TABLE 9

One Liter Scale Processing of Mab Using Various Phase Systems Followed by Protein A Affinity Chromatography.

| System | 1 | 2 | 3* | 4 | 5** | 8 |
|---|---|---|---|---|---|---|
| % EOPO | 8 | 8 | 8 | 12 | 8 | 8 |
| [PO4] mM | 200 | 0 | 0 | 0 | 200 | 0 |
| [Citrate] mM | 0 | 100 | 250 | 100 | 0 | 200 |
| pH | 8 | 7 | 7 | 7 | 8 | 7 |
| Temp | 40 | 40 | 20 | 40 | 40 | 40 |
| mM NaCl | | | 150 | | | |
| System Compounding | | | | | | |
| mL water phase | 650 | 650 | 550 | 520 | 690 | 680 |
| gram of 100% EOPO | | | | | 64 g | |
| mL 0.8M NaP, pH 8, =[200] mM | 200 | | | | | |
| g Na2HP, =[200] mM pH 8 | | | | | 25.7 g | |
| g NaH2P, =[200] mM pH 8 | | | | | 2.1 g | |
| mL 0.8M NaCit, pH 7, =[100 or 250] mM | | 100 | 250 | 100 | | 200 |
| g NaCl | 0 | 0 | 6.96 | 0 | 0 | 0 |
| ml Feed added | 440 | 540 | 390 | 460 | 736 | 440 |
| ml Total Volume | 800 | 800 | 800 | 800 | 800 | 800 |
| Phase vol. ratio (water-rich phase/polymer-rich phase) | 4.3 | 4.6 | 1.45 | 1.9 | 5.6 | 5.5 |
| Mixing and Phase Separation Time (h) | 0.5 | 1.5 to 2 | 3 | 0.5 to 1.5 | 1.5 to 2 | 1.5 |

EOPO refers to Breox 50 A 1000.
*Under these high salt conditions phase formation occurs at RT with phase density inversion so the Mab containing water-rich phase is the bottom phase.
**In this experiment the polymer and salts were added as solids, which necessitated a longer time for mixing and separation.

It can be seen that these 800 mL systems showed phase separation over various times from 30 to 120 minutes. It should be noted that phase separation depends on phase system height (depth) more than on volume so that a 1 L system with 20 cm height may phase separate in same manner as 500 L system with 20 cm height. This is important as 500 L system with 20 cm height can be processed in a container with radius of 90 cm.

Protein A Chromatography

The chromatography was performed using a 5 ml HiTrap MabSelectSure. Analysis was performed using a 1 ml HiTrap MabSelectSure column and a Superdex 200 5/150 GL. Sample was 50 ml Feed or water-rich phase, Buffer A: 20 mM sodium phosphate in 0.15 M NaCl, pH=7.2, Buffer B: 50 mM sodium citrate pH=3.0. Flow 5 ml/min (150 cm/h) and gradient 0-100% step. Flow through and eluate were collected for further analysis of mAb, HCP and aggregate levels. The water-rich phases were centrifuged before applied to the subsequent chromatographic step in order to make recovery estimates and other analyses more accurate (not related to large aggregates which could be fouled on the column). As such this centrifugation step was taken to be the equivalent of depth filtration prior to chromatography.

Analysis of the Samples

Concentration of mAb was measured using a MabSelectSure column. 50 ul samples were applied to a 1 ml HiTrap MabSelectSure column. The area of the eluate peak was integrated and multiplied with the feed and water phase volume respectively. The recovery for the extraction using the ATPS was calculated by comparing the total number of area units. The recovery of mAb for the MabSelectSure step was calculated in the same way. Sample: 50 ul feed or water phase,
Column: 1 ml HiTrap MabSelectSure,
Buffer A: PBS, Buffer B: 100 mM sodium citrate pH=3.0, Flow 1 ml/min (150 cm/h)
Gradient: 0-100% B, step.

Dimer and aggregate (and also the MAb concentration) was measured using a Superdex 200 5/150 GL gel filtration column. The area of the dimer- and monomer peak were integrated automatically by the UNICORN software. The total area of the dimer from the feed and the water phase was compared. Sample: 50 ul feed or water phase, Column: 3 ml Superdex 200 5/150 GL, Buffer: PBS, Flow 0.3 ml/min (45 cm/h).

Results

Figure 7:
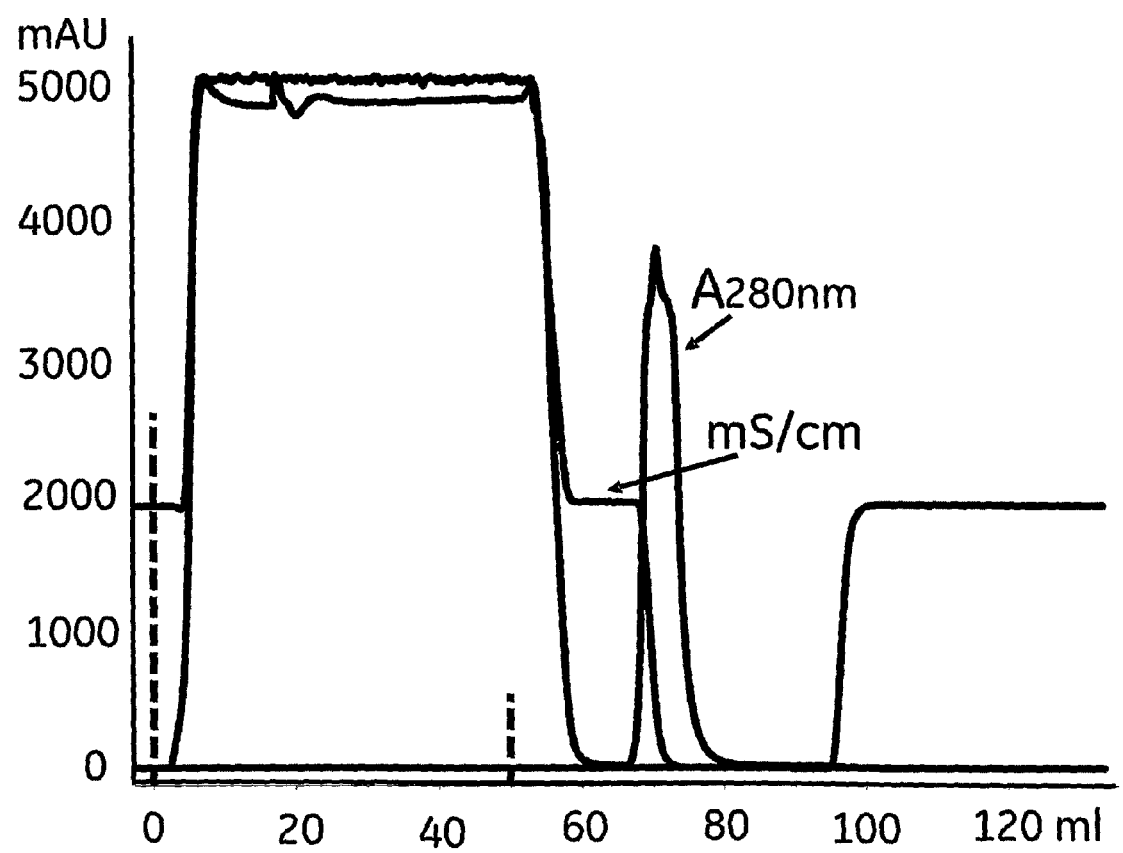
FIG. 7. Chromatogram showing the MabSelect Sure affinity capture of mAb from the water-rich upper phase of System 4 in Table 9. The eluate peak was automatically integrated. Column was a standard HiTrap™ 5 ml bed volume column run under standard conditions.

It was possible to apply the water phase directly on to the MabSelectSure column without any dilution or alteration of pH or conductivity (FIG. 7).

Figure 8:
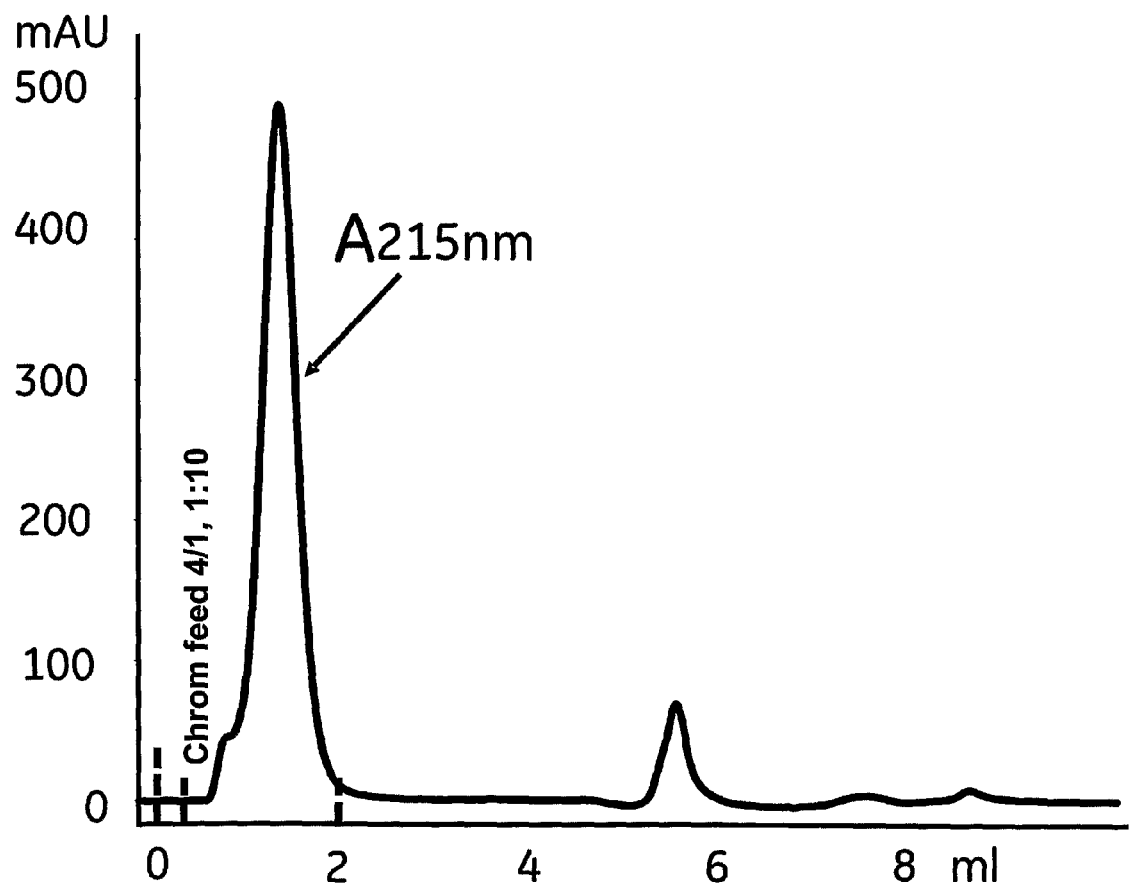
FIG. 8. MabSelect Sure affinity chromatographic analysis of Mab-concentration in the feed showing presence of monoclonal antibody (Mab) indicated by the smaller peak. The second $A_{215\,nm}$ peak is the Mab. Standard 1 ml HiTrap column was used under normal MabSelect operating conditions.

Analysis of the mAb-concentration from the feed and water phase was done using a MabSelectSure column (FIG. 8). In FIG. 8 the crude feed was analyzed. As can be seen most of the protein and other 280 nm UV-absorbing compounds pass right through the column.

Figure 9:
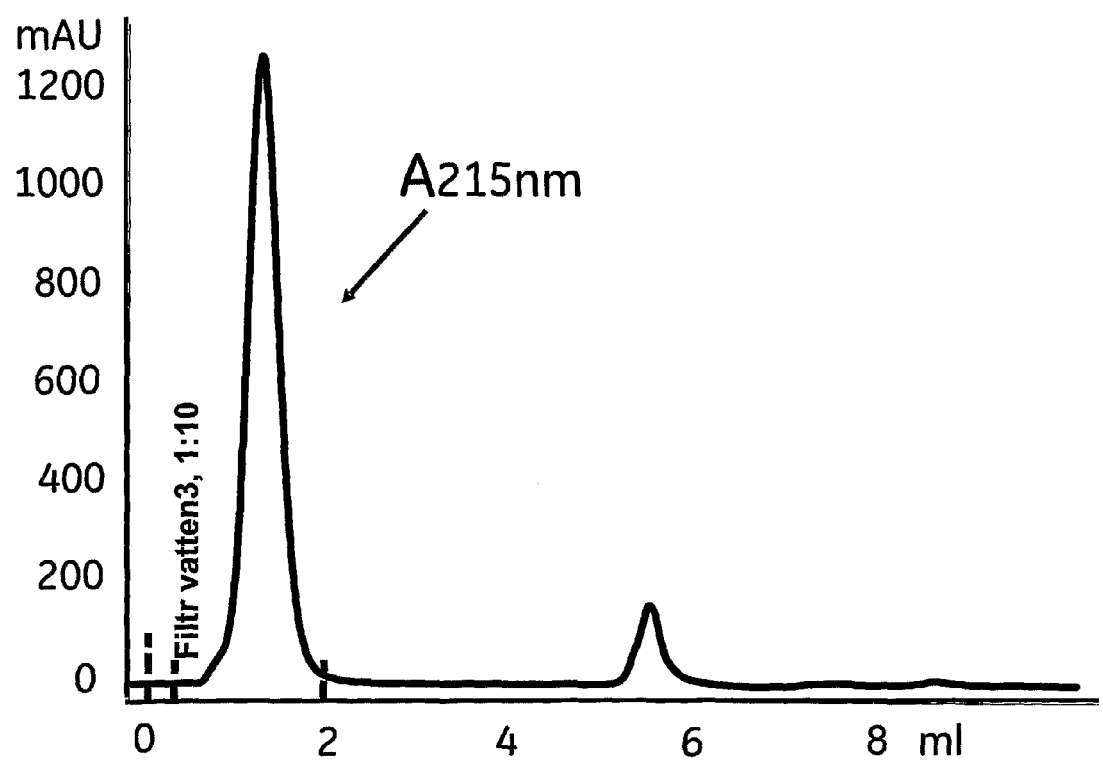
FIG. 9. MabSelect column based analysis of the mAb concentration in a typical water-rich phase, exemplified by system 3 upper phase (Table 9 and 10) (compare with FIG. 8). The second $A_{215\,nm}$ peak is the mAb-containing eluate. A standard 1 ml HiTrap column was used under normal MabSelect operating conditions.
Figure 10:
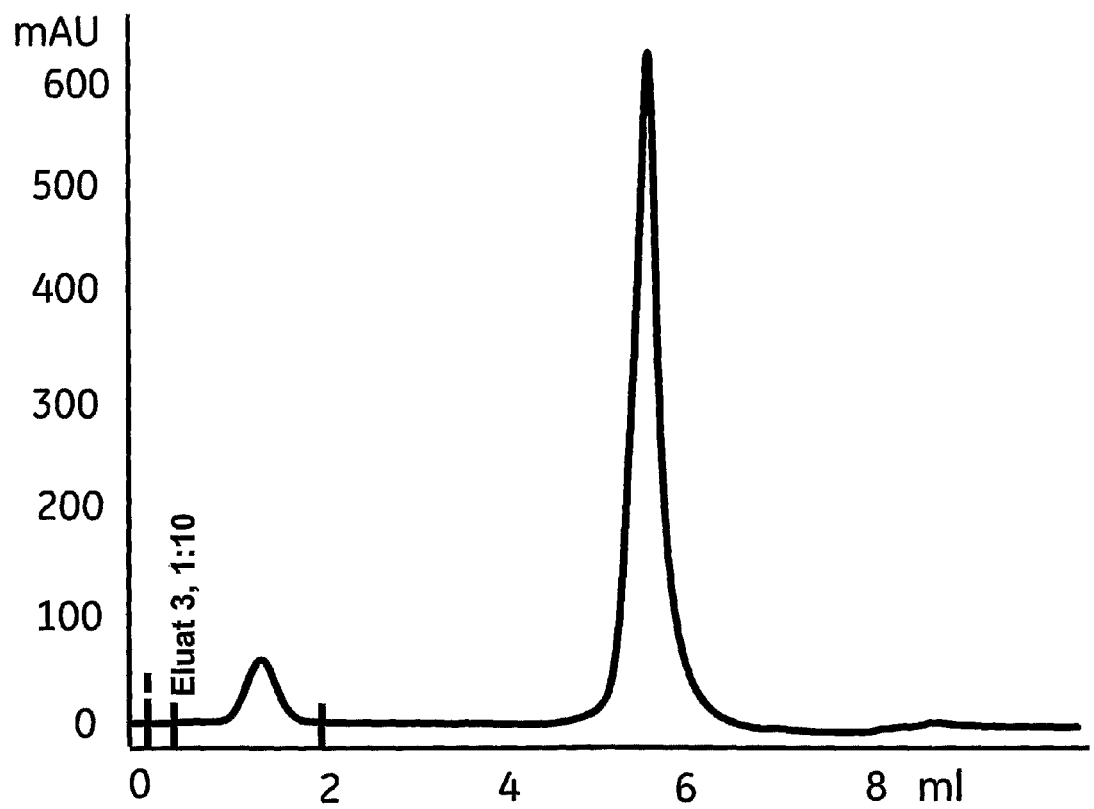
FIG. 10. MabSelect affinity column based analysis showing Mab in concentrated and apparently native form following partitioning and affinity purification on MabSelect Sure, exemplified with the sample system 3 upper phase (see Table 9 and 10). For this analysis a standard 1 ml HiTrap column was used under normal MabSelect operating conditions.

FIG. 9 shows the analysis of the mAb-concentration for the System 3 upper phase (Table 9). This chromatogram is similar in general shape to FIG. 8, which was expected. FIG. 10 shows affinity analysis of elutate sample related to upper phase being passed through an affinity column. Compared with FIGS. 8 and 9 one can see the concentrating effect of the affinity column on the Mab (second peak).

Table 10 shows the results from the various runs in Table 9. It shows that Mab recovery from the two-phase extraction was >95% for all cases except one. Under the conditions studied and with this Mab sample the two-phase extraction did not contribute much to the reduction of HCP which was less than 10%. However the system was chosen in this case to optimize Mab recovery. There was no apparent reduction in aggregate-concentration judging that the ratio between monomer and dimer was unchanged.

Table 10 also provides a summary of the results from the MabSelect Sure runs i.e. the eluate from the MabSelectSure column has been compared to the starting material. The start material was either feed or the different target containing water-rich phases. As expected the recovery was almost 100% and the reduction of HCP was >99%. The reduction of dimer/aggregate is uncertain and might be within the variation of the analytical method. Comparing the ratio dimer/ monomer in feed and eluate from this step, there is a difference. In the feed, before the MabSelectSure step, the ratio is 0.17, compared to 0.14-0.15 after the MabSelect Sure step.

After the MabSelectSure step there was a big reduction, as expected, in HCP. Recovery has been measured by two methods, the "Sure"-method and by gel filtration respectively.

TABLE 10

Analysis of Mab Target Containing Feed, Water-Rich Phases, and MabSelect Sure Affinity Chromatography Elution Peaks.

| | | Feed | System Water Rich Phase* | | | | | |
|---|---|---|---|---|---|---|---|---|
| | | | 1 | 2 | 3+ | 4 | 5 | 6 |
| A | Phase vol. (ml) | | 650 | 650 | 550 | 520 | 690 | 680 |
| B | HCP (ng/ml)** | 39405 | 29415 | 34410 | 26640 | 32190 | 38295 | 25530 |
| C | HCP (ppm) | 26096 | 25358 | 25872 | 22200 | 23496 | 28367 | 22009 |
| D | Mab (mg/ml) | 1.51 | 1.16 | 1.33 | 1.20 | 1.37 | 1.35 | 1.16 |
| E | Mab Recovery (by MabSelect) | 100 | 97 | 100 | 100 | 98 | 78 | 98 |
| F | Mab Recovery (by SEC Superdex) | 100 | 101 | 93 | 93 | 93 | 89 | 97 |
| G | Dimer % from SEC | 17 | 16 | 19 | 17 | 20 | 24 | 16 |
| | | | Post MabSelect Sure | | | | | |
| H | Mab (mg/ml) | 5.32 | 3.53 | 3.67 | 3.33 | 3.76 | 4.68 | 1.89 |
| I | Mab Recovery (%) | 99 | 106 | 96 | 97 | 98 | 137 | 76 |
| J | HCP (ng/ml) | 257 | 354 | 221 | 130 | 200 | 260 | 120 |
| K | HCP (ppm) | 48 | 100 | 60 | 39 | 53 | 56 | 64 |
| L | Dimer % from SEC++ | 15 | 14 | 14 | 14 | 14 | 15 | 18 |

*Systems correspond to Table 9. Total system volume 800 ml in all cases.
+System 3 formed two phases at RT but exhibited phase inversion so the Mab target containing, water-rich phase was the lower phase.
**Feed HCP at 39405 ng/ml corresponded to 26096 ppm. System 1 water-rich phase HCP of 29415 corresponded to 25358 ppm. MabSelect Sure affinity chromatography recovery of Mab when loaded with water rich phase from system 5 was 137% and from system 6 was 76%. Typical values are 100%.
++In this analysis there is no distinction between dimer and larger aggregates. Multiplying the Ratio by 100 gives the percent value of dimer content compared to the monomer content. Analysed by size exclusion (gel filtration) chromatography (SEC). Monomer concentration calculated from a standard curve, giving the equation y = 663x − 3, r = 0.995.

In regard to analysis of results concentration of mAb was measured using a MabSelectSure column run an Akta chromatography unit (GE Healthcare). 50 μl samples were applied to a 1 ml HiTrap MabSelectSure column. Buffer A was 150 mM NaCl, 10 mM NaPhosphate pH 7.2 (PBS), Buffer B was 100 mM sodium citrate pH 3, flow 1 ml/min (150 cm/h) with gradient 0-100% B, step. The area of the eluate peak was integrated and multiplied with the feed- and water phase volume respectively. The recovery for the extraction using the ATPS was calculated by comparing the total number of area units.

The recovery of mAb for the MabSelectSure step (following partitioning) was calculated in the same way. In some cases dimer and aggregate (and also the MAb concentration) was measured using a Superdex 200 5/150 GL gel filtration column. The area of the dimer- and monomer peak were integrated automatically by the UNICORN software. The total area of the dimer from the feed and the water phase was compared. Sample 50 μl feed or water phase, column 3 ml Superdex 200 5/150 GL, Buffer A PBS, flow 0.3 ml/min (45 cm/h). Host Cell Proteins (HCP) was measured using Gyro-Lab.

Two results are easy to identify as outliers e.g. when the recovery is more than 110% (elutate system 5) and when it is 76% for elutate system 8. Many years of experience suggest the recovery should always be close to 100% with all of the Protein A media under the conditions run.

Comparing the HCP-content in the water phase and the start material (Table 10) there is a small reduction in the relative HCP-concentration i.e. the ATPS reduces the HCP-content. When it comes to the dimer/aggregate reduction, some of the ATPS seemed to have slightly increased the concentration of dimers. The differences are small and they might be within the spread of the analytical method.

There is a difference between them but both methods showed a high recovery from the phase systems and the follow on Protein A.

Example 11

Partition of Fab in NaPhosphate and NaCitrate Based ATPS

It is assumed that Mab proteins tend to favor the water-rich phase in EOPO and water ATPS's containing salts such as phosphate or citrate due to their relative hydrophobicity and their typically net positive charge. Given that GFP, which is quite hydrophobic, also shows high K values size may, as predicted by Brønsted equation, play a secondary role. That prediction is born out the inability of the systems to differentially partition molecular aggregates, dimers and monomer Mab forms (see above). Fortunately it also suggests that partition may also be suitable for antibody Fab fragment proteins (Fabs). Partition of a polyclonical Fab (pI: 5.5-9.5) of approx. 55 kDa MW was tested in EOPO-ATPS based on NaPhosphate and NaCitrate buffers by addition of 0.5 mg Fab to each system during the system preparation. After phase formation at 40 degrees C. the phases were separated and absorbance of each phase was monitored at 280 nm by spectrophotometer. The partition coefficient (K) and the % concentration of each Fab in the upper phase (C/Co)×100% were calculated (see Table 11). The result showed that the recovery of Fab in the water phase based on NaCitrate buffer was higher (79%) than in the similar phase based on NaPhosphate buffer (60%). These partition values are lower than is typical for the Mabs and polyclonal Ig noted in this report. However the systems studied were optimized for Mabs and not Fabs. In addition the Fab sample apparently contained some proteins whose pI was quite acidic so it not surprising their partition K values may be lower.

TABLE 11

Partition of Fab in NaPhosphate and NaCitrate based ATPS

| System | $A_{280}$ and Vol. Upper | $A_{280}$ and Vol. Bottom | Volume Ratio | K ($A_{280}$ Up/$A_{280}$ Bot) | C/Co × 100% |
|---|---|---|---|---|---|
| 8% EOPO, 200 mM NaP pH 7.4, 150 mM NaCl | 0.12 (4.2 ml) | 0.41 (0.8 ml) | 5.25 | 0.29 | 60% |
| 8% EOPO, 100 mM NaP pH 7.4, 150 mM NaCl | 0.22 (4.1 ml) | 0.27 (0.9 ml) | 4.55 | 0.81 | 79% |

Example 12

Protein Selectivity in the EOPO Based ATPS

Proteins with different pI were partitioned at 40 degrees C. in 5 ml system containing 8% EOPO, 200 mM NaPhosphate, pH 7.4 and 150 mM NaCl. The total protein concentration in the systems was 1 mg/ml. After phase formation the phases were separated and absorbance of each phase was monitored at 280 nm by spectrophotometer. The partition coefficient (K) calculated and summarized in Table 12. The results suggest that the basic proteins were partitioned totally in the water phase while the most acidic protein was partitioned between the both upper and lower phase. Even though the polyclonal Ig sample had mean pI of approximately 7 it exhibited (as previously noted) high k values; perhaps due to hydrophobicity and size.

TABLE 12

Protein partitioning in EOPO-ATPS at pH 7.4

| Protein (All Sigma except Ig from Octapharma) | pI | Volume ratio (Up/Bot) | A280 × ml (Upper vol.) | A280 × ml (Bott. Vol.) | K = A280 (Upp/Bott) |
|---|---|---|---|---|---|
| Pepsin (P-6887) | 2 | 4.8 | 4.06 | 1.87 | 2.2 |
| Alpha-lactalbumin (L-6010) | 4.2 | 4.8 | 14.3 | 0.2 | 70 |
| BSA (A-7638) | 5.6 | 4.8 | 2.65 | 0 | >200 |
| Myoglobin (M-1882) | 7 | 4.8 | 6.51 | 0 | >200 |
| Trypsinogen (T-1143) | 9.3 | 4.8 | 10.74 | 1.15 | 9.3 |
| Lysozyme (L-6876) | 11 | 4.8 | 12.9 | 0 | >200 |
| GammaNorm (Octapharma) | ~7 | 4.8 | 6.89 | 0 | >200 |

The partition should be related to both hydrophilic nature (net charge per unit area with positive proteins favoring the water-rich phase) and the hydrophobicity (more hydrophobic proteins in the water rich phase as self associated EOPO phase excludes them). The system studied contained significant NaPhosphate and NaCl and therefore it may not be surprising that most of the proteins showed significant upper phase partition. However even with such a system some selectivity was demonstrated. Based on other results noted here decreasing NaCl and NaPhosphate to 100 mM NaCl and increasing the pH to 8 may decrease K values for alpha lactalbumin, BSA and myglobin and lead to a more selective system. However such a system might not offer the best recovery for targets such as antibodies. In cases where lower partitioning proteins are the target proteins their partition may be increased by alteration of salt, pH, inclusion of hydrophobic affinity ligands or other variables documented in the above examples.

Example 13

Formation of Two Phase Systems with Milk or Blood

Possibility to use two-phase systems with variety of complex biological related samples such as recombinant or native proteins in plants, milk, blood, etc. led to studies to see if milk or blood based solutions could be processed. In the experiments involving milk four conditions were screened for two-phase formation (see Table 13). It was noted that phase systems formed in some conditions but that phase formation was complicated by presence of fatty substances as well as (possibly) by high calcium levels. Latter is known to be able to chelate with the oxy polymers and phosphate to form precipitates such as formed when calcium chloride is added to PEG in phosphate buffered saline. Results suggest the process will work better with skim milk.

TABLE 13

Formation of Two Phase Systems with Milk.

| System (5 ml) | ml milk in the system | Phase formation | ml Upper Phase | ml Bottom Phase |
|---|---|---|---|---|
| 8% EOPO, 0 mM NaPhosphate, pH 7.4 and 0 mM NaCl, 40° C. | 2.6 | – | – | – |
| 8% EOPO, 100 mM NaPhosphate, pH 7.4 and 150 mM NaCl, 40° C. | 2.6 | + | 2 (aggregate observed) | 3 (turbid) |
| 20% EOPO, 0 mM NaPhosphate, pH 7.4 and 0 mM NaCl, 40° C. | 2.6 | + | 4.6 (turbid) | 0.4 (clear) |
| 20% EOPO, 100 mM NaPhosphate, pH 7.4 and 150 mM NaCl, 40° C. | 2.6 | + | 2 (aggregate observed) | 3 (ppn. observed) |

Experiments involving blood were performed by adding Breox 50A EOPO polymer stock and NaCitrate pH 7.4 stock to 7 ml blood (which naturally contains approx. 150 mM NaCl) to generate an approximately 70% (v/v) blood isotonic solution at 10% EOPO and volume 10 ml in 15 ml capped plastic conical tubes. Following gentle hand inversion mixing at 37° C. the mixture separated within ten minutes into two liquid phases and a region of cells. Good phase formation, clarification and phase separation were seen with blood samples handled in this manner (data not shown).

Example 14

Formation of Two Phase Systems with Pluronic L81

Breox and Ucon polymers are random copolymers of EO and PO. Pluronics are coblock polymers of the form $(EO)_x(PO)_y(EO)_x$. To investigate the recovery of Mab in ATPS based on Pluronic L81 polymers (10% EO & 90% PO with total polymer MW of approx. 2700), some experiments were performed with different salt types (phosphate and citrate) using Mab feed 2. Pluronic L81 has a lower Tc than the Breox polymer used in most of the above studies and may be suitable for use at room temperature. Two phase systems were formed at room temperature when the polymer concentration was 10-20% indicating that other thermoresponsive clouding polymers may also be suitable for use in the manner of the invention. Mab (feed 2) recovery in the water-rich phases was measured using MabSelect Sure analysis. ATPS based on EOPO was used as control. The results are presented in Table 14 and show Mab recoveries of above 92% for the EOPO systems and above 86% for (unoptimised) L-81 systems.

TABLE 14

Mab partition in ATPS systems of Breox or Pluronic L81 polymers.

| Sample or Biphase System | Water-rich phase (w/Mab) | Mab (mg/ml) | Phase vol. (ml) | Total Mab (mg) | Mab Recovery % |
|---|---|---|---|---|---|
| Mab Feed 2 | | 0.46 | 2.29 | 1.06 | 100 |
| 8% Breox, 100 mM NaCit. pH 7 and 1150 mM NaCl, 40° C. | Upper | 0.25 | 4.15 | 1.05 | 99 |
| 8% Breox, 200 mM NaCit. pH 7 and 150 mM NaCl, 40° C. | Upper | 0.24 | 4.15 | 0.98 | 92 |
| 8% Breox, 250 mM NaCit. pH 7 and 150 mM NaCl, 22° C. | Bottom** | 0.37 | 3.10 | 1.14 | 108 |
| 10% L81, 100 mM NaPhospate. pH 7.4 and 150 mM NaCl, 22° C. | Upper | 0.29 | 3.40 | 1.00 | 95 |
| 10% L81, 100 mM NaCit. pH 7 and 150 mM NaCl, 22° C. | Bottom** | 0.28 | 3.2 | 0.91 | 86 |

Some 5 ml total volume systems compounded with Breox 50A 1000 EOPO polymer and some with Pluronic L81. Some phase separated at RT and others at 40° C.
**In some cases phase inversion occurred with the water-rich (polymer-poorer) phase becoming the bottom phase.

Example 15

Fourteen Liter Scale Partition in a Disposable Bioreactor

Here we show the use of aqueous two phase system (ATPS) based on Breox (EOPO) polymer added directly in concentrate with salts to a 10 L Mab cell culture in WAVE™ bag to allow cell removal (clarification) without centrifugation at 14 liter scale. Note that in this study the method of adding polymer and salt stocks was chosen to aid ease of mixing, not to optimize volume reduction. So too, the phase system was chosen to effect rapid separation and good Mab recovery. It was not optimized to effect a balance between Mab recovery and host cell protein removal. It was felt that based on the above examples, reagent addition methods and system optimization in regard to removal of HCP and other contaminants would be straight forward if a workable model system could be demonstrated.

The real feed 4 Mab cell culture is expressed in a CHO cell line. Culture duration was 18 days and culture vessel WAVE Bioreactor system 20/50 with a 20 L bag and pH/Oxywell. Culture media was PowerCHO2 (Lonza) with 5 g/L hydrolysate UF8804 (Millipore) and supplied with glucose and glutamine when needed. Feed sample was defined as ready to harvest when the average viability of cells fell below 40%. The contents of the WAVE bag was temperature stabilised 42'C when polymer-salt solution was added.

Figure 11:
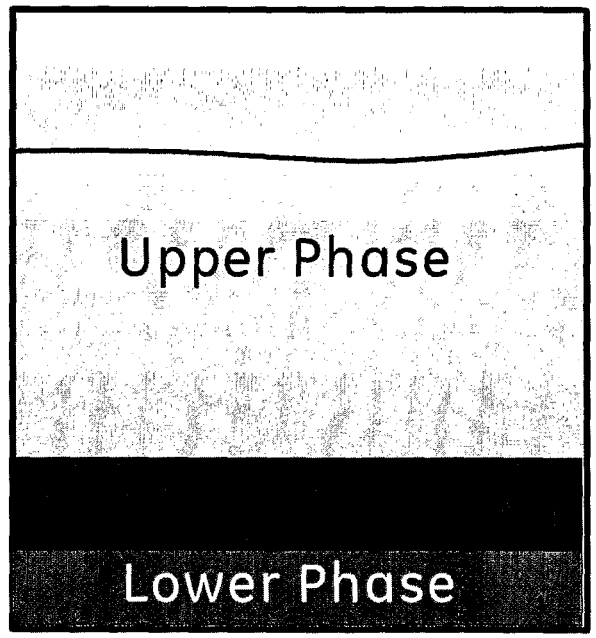
FIG. 11. Formation of two phase system at 40° C. by adding phase forming polymer and salt directly to Wave™ bag containing cell fermentation culture. In this example the bag was placed in the long axis vertical position to aid visualization, and so bed height could mimic that found under larger volume conditions. White cell layer can be seen collecting spontaneously at the phase interface.

An ATPS polymer system was prepared directly by pumping the stock solution mixture into the WAVE bag which contained 9.5 kg Mab feed 4 (see FIG. 11).

TABLE 15

Amounts of the chemicals and feed required to prepare ATPS.

| Stock solution | Amount of stock added (Liter) | Total amount chemicals (Liter) | Feed (kg)* |
|---|---|---|---|
| 50% (w/w) Breox (EOPO polymer) stock | 3.6 | 8.37 | 9.50 |
| 800 mM NaPhosphate, pH 8.0 stock | 4.5 | | |
| 5M NaCl stock | 0.27 | | |

*Assuming 9.5 kg feed = approx 9.5 L. EOPO, 50% (w/w) was prepared by dissolving 2 kg EOPO in 2 kg MQ water.

Figure 12:
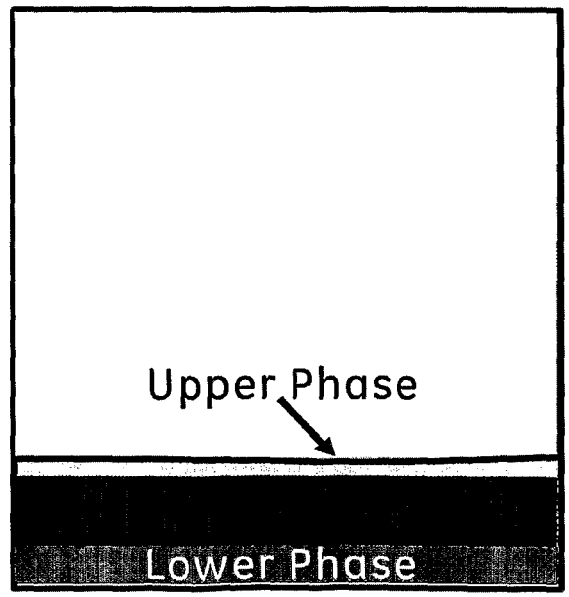
FIG. 12. Isolation of the Mab target containing upper phase by a tube inserted into the Wave™ bag, which in this example is the vertical long axis position. Lower phase was collected via the tube in the lower right corner of bag when in long axis vertical position.

To reach a final concentration of 10% EOPO (w/w), 200 mM NaPhosphate, pH 8.0, and 150 mM NaCl, stock solutions were premixed according to Table 15. Thus a total amount of 8.37 L of this mixture was heated up to 40° C. and was then pumped to the feed material in the WAVE bag, which had almost the same temperature, using a peristaltic pump. The time for pumping the polymer mixture was about 50 min. After leaving the mixture for shaking on the WAVE reactor for about 15 min the WAVE bag including the bag holder was disconnected from the reactor and was then put on a lab bench with long axis in vertical position (see FIG. 11). This aided visualization of phase formation but also allowed bag tubing port to be directed to the bottom and top of the bag. It also adjusted the phase height more in keeping with what might be expected in an even larger process (see discussion above). The formation of two phase system was observed after 5 min and was completed after 30 min. A layer of cell debris was formed in the interface as seen in FIG. 12. The upper phase was then transferred into different bottles by inserting a tube from the upper part of the WAVE bag which was then connected to a peristaltic pump (see FIG. 12). The bottom (polymer) phase was then transferred into bottles using a tube attached to what becomes the bottom corner of the WAVE bag when it is placed long axis vertical (see FIG. 11).

The collected upper phase materials from different bottles were pooled (~13.5 L) and were then filtrated using a 6 inch ULTA 0.6 um GF connected to a 6 inch ULTA HC 0.2 um filter. After filtering of 7 liter material the 6 inch ULTA 0.6 um GF was replaced with a new filter because of increase of the pressure to 2.5 bar. The filtered material was collected in a WAVE bag and was then kept at 4° C.

The recovery of the Mab in the upper polymer poor phase fractions after ATPS was measured using MabSelect Sure analysis (see above). The Mab recovery and host cell protein (HCP) data for crude feed and the recovered Mab after ATPS experiments are presented in Table 16. The results from these experiments showed that Mab was partially purified by ATPS with a recovery of >99% (Table 16) with significant removal of cell debris (FIGS. 11 and 12). No significant reduction of HCP was obtained by the aqueous polymer two phase system used in this experiment (Table 16).

TABLE 16

Mab and HCP Recovery in Wave Upper Phase Recovered Fractions.

| Feed or Upper Phase Fraction | Liquid Weight (kg) | Upper. Phase % total | Mab (mg/ml) | Total Mab (g) | Mab Recover % | HCP (µg/ml) | Total HCP (mg) | HCP (%) |
|---|---|---|---|---|---|---|---|---|
| Feed 4 | 9.500 | | 1.288 | 12.236 | 100 | 31.0 | 294.5 | 100 |
| Fraction 1 | 5.000 | 36.6 | 0.878 | 4.390 | 35.9 | 23.5 | 117.5 | 40 |
| Fraction 2 | 5.000 | 36.6 | 0.914 | 4.570 | 37.3 | 22.5 | 112.5 | 38 |
| Fraction 3 | 2.500 | 18.3 | 0.898 | 2.245 | 18.3 | 22.0 | 55.0 | 19 |
| Fraction 4 | 0.660 | 4.9 | 0.884 | 0.583 | 4.8 | 20.5 | 13.5 | 5 |
| Fraction 5 | 0.500 | 3.7 | 0.772 | 0.361 | 3.0 | 16.0 | 8.0 | 3 |
| Total 1 to 5 | 13.660 | | | 12.149 | 99.3 | | 306.5 | 104 |

Table calculations assume liquid phase densities of approximately 1. Lower, polymer-rich phase was 4.600 Kg with host cell protein (HCP) at 0.45 µg/ml or 2.07 mg total. HCP determined by commercial ELISA kit. Assume the last fraction not complete as all upper phase could not be recovered with the simple methods employed. Data suggests approximately 0.7% or less than 100 ml left.

More than 8 L of polymer solution was pumped to a 20 L WAVE bag containing 9.5 kg of Mab cell culture (feed 4). The formation of two phase system was already observed after 5 min and was completed after 30 min. A layer of cells and debris was formed in the interface. The ATPS the cells and debris was successfully removed and the target Mab protein was almost completely recovered in an aqueous upper phase. In same manner as for smaller scale studies with real feed, following simple filtration, the clarified Mab-containing phase could be applied directly to a MabSelect affinity column without any loss of Mab or column performance.

Example 16

Virus and Viral Vaccine Processing

General Experimental

Virus related experiments involved applying representative systems from the above antibody fermentation feed and related experiments to experiments related to viral vaccine processing. As such similar polymers, salts, systems and techniques were used. Two example experiments were performed using two strains of virus. The first involved partition using a sucrose gradient purified virus augmented with CHO cell proteins; the second was a real virus feed augmented with clarified and concentrated virus (from the same source).

Chemicals, Reagents and Viral Stocks

Breox™ 50 A 1000[1], MW 3900, See above.

All other chemicals used in this study were of Analytical grade and purchased from MERCK.

[1] The Breox™ used in the present study is common industrial surfactant and is available from several sources. Similar polymers are used in biopharmaceutical processing and formulation where they serve various functions. Breox 50 A 1000 is a random copolymer consisting of 50% ethylene oxide and 50% propylene oxide. Its molecular mass (number average) is 3900 Da and it was obtained by KTH (Dept. of Biotechnology) from International Speciality Chemicals (Southampton, UK) for use in a larger study related to Breox and detergent two phase systems useful for extraction of membrane proteins (see J. Chromatogr. B, vol 711, pp. 53-60, 1998). The Breox family of polymers appear quite safe and biocompatible and are used in some formulations.

Viral Material

Two samples of biological material were used. The first was vaccine augmented CHO cell based feed created by taking MabSelect affinity column (GE Healthcare) flow through (FT) from Chinese hamster ovary (CHO) cell fermentation. The FT contained little or no Mab but standard CHO host cell proteins, and other contaminants. It was enriched with 40% sucrose gradient purified intact virus fraction of A/H1N1/New Caledonia influenza virus, formaldehyde treated, hemagglutinin (HA) concentration ~200 µg/ml.

The second sample, referred to as virus feed, was based on crude harvest of active A/H1N1/Solomon Islands influenza virus (propagated in MDCK cells) with a HA concentration of ~13.8 μg/ml. In order to more easily assay results the virus concentration in the virus feed was increased by adding 9 ml of clarified and concentrated A/H1N1/Solomon Islands influenza virus (~73 μg/ml) to 51 ml of the crude harvest. The virus materials also contained 10 mM TRIS pH 7.4 and 0.15M NaCl.

Partition Methods

Each aqueous two phase system (ATPS) solution was prepared directly in a 15 ml Sarstedt tube by mixing appropriate amounts/volumes of the stock solutions listed below in Table 17. The ATPS was based on 8-12% EOPO system in 100 mm NaP, pH 7 and 150 mM NaCl. After addition of virus feed mixture the final volume of each system was adjusted to 10 ml with PBS (see Table). The mixtures were vortexed about 30 seconds and were then left for phase formation for about 1 h at 40-45° C. in an oven. The formed phases were then separated and analyzed according to methods noted below.

Stock solutions:

BREOX 50 A 1000, 100% (w/w): Used directly.

NaP (Na-phosphate, 0.8 M): pH 7 was prepared by mixing appropriate amounts of 0.8 M $NaH_2PO_4$ and 0.8 M $Na_2HPO_4$.

NaCl (5 M): Prepared by dissolving 14.6 g NaCl in 50 ml MQ water.

TABLE 17

Preparation of 10 ml scale of 8-12% EOPO phase systems containing 100 mm NaP, pH 7, 150 mM NaCl using virus feed mixture.

| Exp. No. | % polymer | polymer 100% (g) | ml NaP 0.8M | ml NaCl 5M | PBS | Virus feed mixture | Total volume ml |
|---|---|---|---|---|---|---|---|
| 1 | 12% EOPO | 1.2 | 1.25 | 0.074 | | 7.5 | 10 |
| 2 | 12% EOPO | 1.2 | 1.25 | 0.074 | | 7.5 | 10 |
| 3 blank | 12% EOPO | 1.2 | 1.25 | 0.074 | 7.5 | | 10 |
| 4 | 10% EOPO | 1 | 1.25 | 0.074 | 0.2 | 7.5 | 10 |
| 5 | 10% EOPO | 1 | 1.25 | 0.074 | 0.2 | 7.5 | 10 |
| 6 blank | 10% EOPO | 1 | 1.25 | 0.074 | 7.7 | 0 | 10 |
| 7 | 8% EOPO | 0.8 | 1.25 | 0.074 | 0.4 | 7.5 | 10 |
| 8 | 8% EOPO | 0.8 | 1,25 | 0.074 | 0.4 | 7.5 | 10 |
| 9 blank | 8% EOPO | 0.8 | 1.25 | 0.074 | 7.9 | 0 | 10 |

Analyses

Partition results with sucrose gradient purified virus augmented CHO cell samples were analyzed using an enzyme linked immunsorption assay ELISA method (TAKARA) which detects intact virus particles. This is in keeping with the CHO FT feed being augmented with virus from intact virus fraction of sucrose density gradient purified sample (above).

Real vaccine feed sample results were analyzed according to standard commercially available assays. Total protein was analyzed by Bradford Assay, Deoxyribonucleic acid (DNA) by qPCR assay (against MDCK cell genomic DNA) and PicoGreen® (Molecular Probes), Host cell protein (HCP) via use of a Biacore™ instrument (GE Healthcare) based surface plasmon resonance (SPR) assay (using rabbit polyclonal Abs against MDCK cells) and virus HA via a Biacore SPR Assay (ref in C. Estmer Nilsson et al, Vaccine 28 (2010) 759-766). The Biacore HA assay detects viral HA proteins and therefore is also sensitive to all other viral and cell debris containing viral related contaminants (HA).

As noted previously the Breox EOPO polymer concentration in the upper phase is approximately 1% (w/w) whereas in the lower phase it is expected to be much higher (e.g. 70%). Effects of hydrophilic polymers such as EO (polyethylene glycol) and dextran on Bradford assay have been researched by several authors including Barbarosa et al. (Protein quantification in the presence of dextran or poly(ethylene glycol) (PEG) and dextran using the Bradford method. Helder Barbosa, Nigel K. H. Slater, João C. Marcos, Analytical Biochemistry 395 (2009) 108-110) who concluded that PEG concentrations above 10% resulted in a substantial decrease in assay sensitivity.

Results and Discussion

Figure 13:
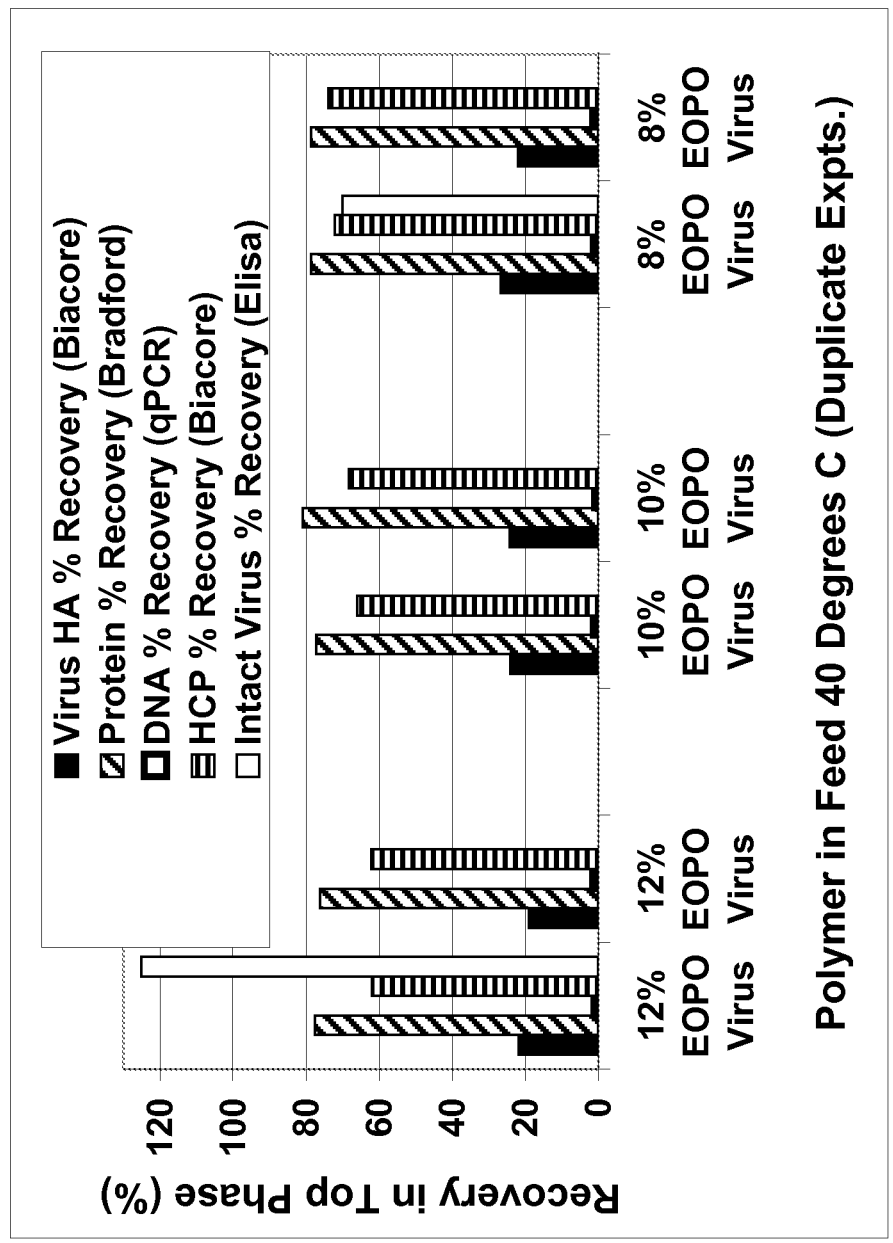
FIG. 13. Recovery of virus and various contaminants in duplicate experiments as function of polymer concentration added.

Three phase systems with different Breox polymer concentrations (8 to 12% w/w) were studied in duplicate experiments. The systems and salt combinations are similar to those studied for protein processing. Two phases readily formed in the feed samples on heating above 40° C. It was difficult to analyse the lower phases due to the high concentration of polymer but the upper phases were readily analysed as were the single phase systems prior to heating. In some cases similar results were obtained with a thermosensitive EOPO block copolymer (e.g. Pluronic® L81) (data not shown). General results are shown in FIG. 13. It can be seen that all three EOPO polymer concentrations real viral feed samples yielded basically similar results with approximately 20% of viral HA in the upper phase by Biacore HA Assay, 60 to 70% of HCP in the upper phase, 70 to 80% of total (Bradford) protein in the upper phase, and less than 5% of DNA in the upper phase. In other experiments where feed was intact sucrose gradient purified virus augmented with cell clarified CHO cell feed, DNA partition to upper phase (measured by PicoGreen® assay) was 70% while upper phase partition of intact virus was 70 to 100% analyzed by ELISA assay. DNA partition is in keeping with that noted for EOPO two polymer based systems in WO2004020629.

The data shows that it is possible to effect clarification of viral feed and primary recovery of intact viral particles for further processing, using single responsive polymer two phase system formed in feed. As in the case of Mab processing the upper phase will contain some HCP and some DNA as well as virus but should be amenable to further processing via affinity chromatography or other methods. The experiments suggest significant differences in viral and in DNA partition coefficients depending on the type of assay or feed used. This may, in part, be function of unequal partition of intact virus and viral debris between the phases. The somewhat surprising lack of DNA partition into the upper phase in the samples containing cell and viral debris, may be partially explained by DNA interaction with cell and viral debris causing the DNA to accumulate at the interface with the debris.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

The invention claimed is:

1. A method of isolating a target antibody, in unclarified CHO broth from an aqueous liquid, which method comprises:
   a. combining in a container said unclarified broth with a thermoresponsive hydrophilic polymer, and at least one added salt selected from NaCl, $Na_2PO_4$, $KPO_4$, $NaSO_4$, potassium citrate, $(NH_4)SO_4$, sodium citrate, sodium acetate, ammonium acetate and combinations thereof in a concentration of 100-300 mM;
   b. gently mixing the liquid mixture obtained from (a) under conditions where the thermoresponsive polymer is above its cloud point so that it forms a one thermoresponsive polymer, two-phase system and wherein said target antibody partitions into the phase not enriched in thermoresponsive polymer, while nontarget compounds and particles partition to varying degrees to the phase interface or the thermoresponsive polymer enriched phase;
   c. isolating the target antibody; and wherein the thermoresponsive polymer is an ethylene oxide propylene oxide (EOPO) copolymer.

2. A multistep method of isolating one or more target biomolecules or compounds which comprises a clarification of fermentation or similar biomass containing feed step, wherein the clarification of fermentation or similar biomass containing feed is performed by the method of claim 1.

3. The method of claim 2, further comprising the step of
   iii) recycling the polymer from the polymer-rich phases back into a partition unit operation and wherein the container is the container where the fermentation was carried out.

4. The method of claim 1, wherein the EOPO copolymer ethylene oxide as one of its principal components and exhibits a cloud point between 4 and 100° C.

5. The method according to claim 4, wherein the molecular weights of said polymer is in the range of 900-100,000 Da.

6. The method according to claim 1, wherein the polymer tendency to self-associate in aqueous solution is not primarily thermoresponsive but pH responsive.

7. The method according to claim 1, wherein the total polymer constitutes 4-20% (w/w).

8. The method according to claim 1, wherein the two phase system is an aqueous polymer two phase system comprising 4-20% EOPO.

9. The method according to claim 1, wherein the two phase system is an aqueous polymer two phase system comprising 5-15% EOPO.

10. The method according to claim 1, wherein the pH in step (a) is about neutral.

11. The method according to claim 1, wherein the target antibody is a polyclonal antibody, a monoclonal antibody, or an antibody fragment.

12. The method according to claim 1, wherein the two phases are formed in the presence of a hydrophobe or other affinity ligand showing preference to partition into one phase or the other.

13. The method according to claim 1, wherein the mixing and phase formation is carried out in a plastic bag.

14. The method according to claim 1, further comprising at least one step of liquid chromatography.

15. The method according to claim 14, wherein the liquid chromatography comprises Protein A based affinity chromatography.

16. The method according to claim 14, wherein the liquid chromatography is followed by one or more steps comprising affinity chromatography, ion exchange, hydrophobic interaction chromatography or multimodal ion exchange chromatography.

17. The method according to claim 1, wherein the phase not enriched in polymer is the upper, less dense phase of the two phases.

18. The method according to claim 1, wherein the phase not enriched in polymer is the denser of the at least two phases.

19. The method of claim 1, further comprising the steps of
   i) subjecting the target containing phase to another partition by mixing with fresh complementary phase;
   ii) recovering the target antibody biomolecule from the phase it is enriched in.

20. The method according to claim 1, wherein intact or lysed cells are held at the liquid-liquid interface by interfacial tension.

21. The method according to claim 1, wherein the target containing phase is subjected to further phase partition via.

22. The method of claim 19, wherein the container is a fixed, stationary metal container or a disposable, plastic container where fermentation was carried out.

23. The method of claim 1, wherein the target antibody biomolecule concentration in the aqueous liquid exceeds 10 g/L.

* * * * *